United States Patent
Lanning et al.

(10) Patent No.: US 12,009,544 B2
(45) Date of Patent: Jun. 11, 2024

(54) BATTERY INCLUDING NANOFIBROUS MEMBRANE

(71) Applicant: Lyten, Inc., San Jose, CA (US)

(72) Inventors: Bruce Lanning, Littleton, CO (US); Michael W. Stowell, Sunnyvale, CA (US); Anurag Kumar, Sunnyvale, CA (US); Hossein-Ali Ghezelbash, Santa Clara, CA (US)

(73) Assignee: Lyten, Inc., San Jose, CA (US)

( * ) Notice: Subject to any disclaimer, the term of this patent is extended or adjusted under 35 U.S.C. 154(b) by 704 days.

(21) Appl. No.: 17/219,342

(22) Filed: Mar. 31, 2021

(65) Prior Publication Data

US 2021/0218110 A1    Jul. 15, 2021

Related U.S. Application Data

(63) Continuation-in-part of application No. 16/740,381, filed on Jan. 10, 2020, now Pat. No. 11,555,799.

(51) Int. Cl.
*H01M 50/44* (2021.01)
*H01M 4/86* (2006.01)
(Continued)

(52) U.S. Cl.
CPC ......... *H01M 50/44* (2021.01); *H01M 4/8605* (2013.01); *H01M 4/8657* (2013.01);
(Continued)

(58) Field of Classification Search
CPC .. H01M 50/44; H01M 4/8605; H01M 4/8657; H01M 4/8663; H01M 4/8807;
(Continued)

(56) References Cited

U.S. PATENT DOCUMENTS 7,623,340 B1    11/2009 Song et al.
7,875,219 B2    1/2011  Zhamu et al.
(Continued)

FOREIGN PATENT DOCUMENTS

CN    109428087 A  *  3/2019 ........ H01M 10/0525
JP    2016532566 A    10/2016
(Continued)

OTHER PUBLICATIONS

Fu, J., et al., "Flexible High-Energy Polymer-Electrolyte-Based Rechargeable Zinc-Air Batteries", Advanced Materials; 27(37); pp. 5617-5622; Oct. 2015.
(Continued)

*Primary Examiner* — Daniel S Gatewood
(74) *Attorney, Agent, or Firm* — Paradice & Li LLP

(57) ABSTRACT

In some implementations, a metal air battery includes a metal anode, a cathode, a body, a nano-fibrous membrane (NFM), and a hygroscopic interphase layer disposed between the cathode and the NFM. The cathode may be a carbon-based textured scaffold including a plurality of macroporous pathways to distribute oxygen and water vapor supplied by ambient air throughout the cathode and into interior portions of the body. The NFM may include dry salts to produce a liquid electrolyte when exposed to water vapor delivered by the macroporous pathways of the cathode. The hygroscopic interphase layer may include a plurality of microporous pathways configured to drain excess quantities of the water vapor from the cathode and hydrate the dry salts with the water vapor.

27 Claims, 16 Drawing Sheets

(51) Int. Cl.
*H01M 4/88* (2006.01)
*H01M 12/02* (2006.01)
*H01M 12/06* (2006.01)
*H01M 12/08* (2006.01)
*H01M 50/414* (2021.01)

(52) U.S. Cl.
CPC ....... *H01M 4/8663* (2013.01); *H01M 4/8807* (2013.01); *H01M 12/02* (2013.01); *H01M 12/06* (2013.01); *H01M 12/08* (2013.01); *H01M 50/414* (2021.01); *H01M 2004/8689* (2013.01); *H01M 2300/0002* (2013.01)

(58) Field of Classification Search
CPC ...... H01M 12/02; H01M 12/06; H01M 12/08; H01M 50/414; H01M 2004/8689; H01M 2300/0002; H01M 4/86; Y02E 60/10; C01P 2002/82; C01P 2006/12; C01B 32/152; C01B 32/182; G01N 33/0037; G01N 33/0039; G01N 33/004; G01N 33/0044; Y02A 50/20
See application file for complete search history.

(56) References Cited

U.S. PATENT DOCUMENTS

| | | |
|---|---|---|
| 8,132,746 B2 | 3/2012 | Zhamu et al. |
| 8,936,870 B2 | 1/2015 | Affinito et al. |
| 8,968,924 B2 | 3/2015 | Bosnyak et al. |
| 9,040,201 B2 | 5/2015 | Affinito et al. |
| 9,742,030 B2 | 8/2017 | Wright et al. |
| 2011/0059343 A1 | 3/2011 | McKinney et al. |
| 2013/0115527 A1 | 5/2013 | Au |
| 2013/0122380 A1 | 5/2013 | Visco et al. |
| 2014/0057179 A1 | 2/2014 | Yushin et al. |
| 2014/0255799 A1 | 9/2014 | Anandan et al. |
| 2016/0285110 A1 | 6/2016 | Sun et al. |
| 2016/0207688 A1 | 7/2016 | Sebastian et al. |
| 2019/0288334 A1 | 9/2019 | Wright et al. |
| 2020/0278316 A1 | 9/2020 | Lanning et al. |
| 2021/0226225 A1 | 7/2021 | Lanning et al. |
| 2021/0226302 A1 | 7/2021 | Lanning et al. |

FOREIGN PATENT DOCUMENTS

| | | |
|---|---|---|
| JP | 2020194792 A | 12/2020 |
| KR | 10-2017-0139914 A | 12/2017 |
| WO | 2016/061216 A1 | 4/2016 |

OTHER PUBLICATIONS

Guo, B., et al., "Hierarchical N-Doped Porous Carbons for Zn-Air Batteries and Supercapacitors", Nano-Micro Letters; 12(1); p. 20; Jan. 1, 2020.

Kim, J. et al., "Improved Cycling Performance of Lithium-Oxygen Cells by Use of a Lithium Electrode Protected with Conductive Polymer and Aluminum Fluoride", ACS Applied Materials & Interfaces; vol. 8; Nov. 9, 2016; pp. 32300-32306.

Zhang, H. et al., "Three-dimensional bicontinuous ultrafast-charge and -discharge bulk battery electrodes", Nature Nanotechnology; 6(5); pp. 277-281; May 2011.

Zhang, J., et al., "3D-printed functional electrodes towards Zn-Air batteries", Materials Today Energy; 16; p. 100407; Jun. 1, 2020.

International Search (Partial) w/PCT/ISA/206 Inv. To Pay Addl. Fees dated Jul. 12, 2022, for PCT Application No. PCT/US2022/021275; 16 pages.

Zhong, M. et al., "A review of cathode materials and structures for rechargeable lithium-air batteries", Energy & Environmental Science, vol. 8, No. 8; Jun. 4, 2015; pp. 2144-2198.

International Search Report and Written Opinion dated Mar. 14, 2023, for PCT Appl. No. PCT/US2022/037905; 17 pages.

\* cited by examiner

BATTERY INCLUDING NANOFIBROUS MEMBRANE

CROSS-REFERENCE TO RELATED APPLICATIONS

This application is a continuation-in-part application and claims priority to U.S. patent application Ser. No. 16/740,381, filed on Jan. 10, 2020 and entitled "MULTI-PART NONTOXIC PRINTED BATTERIES," which is assigned to the assignee hereof. The disclosures of all prior Applications are considered part of and are incorporated by reference in this Patent Application.

TECHNICAL FIELD

This disclosure relates generally to an air battery and, more specifically, to a metal air battery that can be selectively activated by a user.

BACKGROUND

Miniaturization of electronic devices has resulted in new devices that are aesthetically pleasing, thin, lightweight, and compact. These devices may take advantage of advancements in battery technology that have led to the development of smaller, lighter, and longer-lasting batteries. As the demand for smaller, lighter, and longer-lasting batteries continues to increase, there is a need for even smaller batteries that can deliver more power at lower costs.

SUMMARY

The systems, methods, and devices of this disclosure each have several innovative aspects, no single one of which is solely responsible for the desirable attributes disclosed herein.

One innovative aspect of the subject matter described in this disclosure can be implemented as a metal air battery that includes a body, a metal anode, a cathode, and a barrier layer. The metal anode may include one or more of magnesium, zinc, or aluminum, and may be disposed on a first surface of the body. The body may contain an electrolyte. The cathode may be formed within a second surface of the body opposite the first surface, and may be a carbon-based textured scaffold including a plurality of macroporous pathways configured to distribute oxygen and water vapor supplied by ambient air throughout the cathode and into interior portions of the body. In one implementation, the carbon-based textured scaffold has a surface area greater than approximately 1,000 $m^2/g$. The barrier layer may be removably disposed over the cathode. In some implementations, the barrier layer may prevent the ambient air from entering the interior portions of the body through the plurality of macroporous pathways of the carbon-based textured scaffold when the barrier layer is disposed over an exterior surface of the cathode and seals the plurality of macroporous pathways. In some aspects, removal of the barrier layer from the exterior surface of the cathode can activate the metal air battery by allowing the ambient air to enter the cathode and the interior portions of the body through the plurality of macroporous pathways. In some instances, the barrier layer may be removed by peeling the barrier layer off of the cathode.

The carbon-based textured scaffold may include a plurality of catalytic sites that can participate in oxidation chemical reactions and/or reduction chemical reactions. In some instances, the plurality of catalytic sites are doped with manganese, manganese oxide (MnO), and platinum. The plurality of macroporous pathways may be defined within an outer region of the cathode. A selected number of the macroporous pathways may include or may be associated with a corresponding pore formed in an exterior surface of the cathode. In some instances, the pores may have a diameter of approximately 50 nanometers. In other instances, the pores may have a diameter greater than approximately 50 nanometers. In some implementations, the carbon-based textured scaffold also includes a plurality of mesoporous pathways defined within an inner region of the cathode. The plurality of mesoporous pathways may be interconnected with the plurality of macroporous pathways, and may drain excess water vapor from the cathode. In some instances, the mesoporous pathways may have a diameter between approximately 2 and 30 nanometers. In one or more implementations, the mesoporous pathways may be defined by a plurality of N-doped graphene particles fused together. In some aspects, the inner region of the cathode may also include a plurality of microporous pathways interconnected with the mesoporous pathways and interconnected with the macroporous pathways.

In various implementations, the battery may also include a nano-fibrous membrane (NFM) disposed between the cathode and the metal anode. The NFM may be coated with a layer of carbon-based particles including one or more of $sp^3$ diamond-like carbons or $sp^2$ graphene. In some instances, the layer of carbon-based particles may be the carbon-based textured scaffold of the cathode. In some implementations, the NFM may be a metal-organic framework (MOF) including poly(vinyl alcohol) (PVA), polyamide (PA), micro-crystalline cellulose (MCC), or any combination thereof. In other implementations, the NFM may be formed of Chitosan or carboxymethyl cellulose (CMC).

The NFM may contain one or more dry salts that can produce a liquid electrolyte when exposed to or hydrated by water vapor. The NFM may also include hygroscopic agents to absorb water vapor delivered by the porous pathways of the cathode. In some instances, the dry salts may include one or both of sodium hydroxide (NaOH) or potassium hydroxide (KOH). The hygroscopic agents may include one or more of glycerin/glycerol ($C_3H_8O_3$), ethanol ($C_2H_5OH$), methanol ($CH_3OH$), concentrated sulfuric acid ($H_2SO_4$), or concentrated sodium hydroxide (NaOH). In some aspects, the cathode may transport ions produced in the electrolyte in response to chemical reactions between the oxygen and the water vapor supplied by the ambient air. The ions may include hydroxide (OH—) ions, zincate ($Zn(OH)_4^{2-}$) ions, or any combination thereof.

In some implementations, the metal air battery may also include a hygroscopic interphase layer disposed between the cathode and the NFM. The hygroscopic interphase layer may include a plurality of microporous pathways that can drain an excess quantity of water vapor accumulated at or within the cathode and hydrate the dry salts in the NFM with the water vapor. In some instances, a liquid electrolyte may be dispersed within the hygroscopic interphase layer. In various aspects, the hygroscopic interphase layer may have a thickness between approximately 2 and 10 nanometers.

Another innovative aspect of the subject matter described in this disclosure can be implemented as a battery including a metal anode and a cathode disposed on opposite sides of a body. The battery may also include a nano-fibrous membrane (NFM) disposed between the cathode and the metal anode, and a hygroscopic interphase layer. The body may be defined by the metal anode and the cathode. The cathode may be a carbon-based textured scaffold including a plurality of macroporous pathways that can distribute oxygen and water vapor supplied by ambient air throughout the cathode and into interior portions of the body. In one implementation, the carbon-based textured scaffold may have a surface area greater than approximately 1,000 m²/g.

The NFM may include one or more dry salts that can produce a liquid electrolyte when exposed to or hydrated by water vapor supplied by the ambient air via the macroporous pathways of the cathode. The NFM may also include hygroscopic agents that can absorb water vapor and hydrate the salts contained in the NFM. The hygroscopic interphase layer may be disposed between the cathode and the NFM, and may include a plurality of microporous pathways that can drain excess quantities of the water vapor from the cathode and hydrate the one or more dry salts with the water vapor. The NFM may be coated with a layer of carbon-based particles including one or more of $sp^3$ diamond-like carbons or $sp^2$ graphene. In some instances, the layer of carbon-based particles may be the carbon-based textured scaffold of the cathode.

In various implementations, the NFM may be a metal-organic framework (MOF) including poly(vinyl alcohol) (PVA), polyamide (PA), micro-crystalline cellulose (MCC), or any combination thereof. In some implementations, the NFM may be formed of Chitosan or carboxymethyl cellulose (CMC). The dry salts may include one or both of sodium hydroxide (NaOH) or potassium hydroxide (KOH), and the hygroscopic agents may include one or more of glycerin/glycerol ($C_3H_8O_3$), ethanol ($C_2H_5OH$), methanol ($CH_3OH$), concentrated sulfuric acid ($H_2SO_4$), or concentrated sodium hydroxide (NaOH). In some instances, the cathode may guide transport of one or more ions produced in the liquid electrolyte in response to chemical reactions between the oxygen and water vapor supplied by the ambient air. In some aspects, the ions may include hydroxide (OH—) ions, zincate ($Zn(OH)_4^{2-}$) ions, or any combination thereof.

The carbon-based textured scaffold may include a plurality of catalytic sites that can participate oxidation chemical reactions and/or reduction chemical reactions. In some instances, the catalytic sites may be doped with manganese, manganese oxide (MnO), and platinum. The plurality of macroporous pathways may be defined within an outer region of the cathode. A selected number of the macroporous pathways may include or may be associated with a corresponding pore formed in an exterior surface of the cathode. In some instances, the pores may have a diameter of approximately 50 nanometers. In other instances, the pores may have a diameter greater than 50 nanometers. In some implementations, the carbon-based textured scaffold may also include a plurality of mesoporous pathways defined within an inner region of the cathode. The plurality of mesoporous pathways may be interconnected with the plurality of macroporous pathways, and may be used to drain excess water vapor from the cathode. In some instances, the mesoporous pathways may have a diameter between approximately 2 and 30 nanometers. In some other instances, the mesoporous pathways may be defined by a plurality of N-doped graphene particles fused together. In one implementation, the inner region of the cathode may also include a plurality of microporous pathways connected to the mesoporous pathways and interconnected with the macroporous pathways. In some aspects, the hygroscopic interphase layer may have a thickness between approximately 2 and 10 nanometers, the inner region of the cathode may have a thickness between approximately 0.1 and 50 microns, and the outer region of the cathode may have a thickness between approximately 10 and 50 microns.

The battery may also include a barrier layer removably disposed over an exterior surface of the cathode. The barrier layer may prevent ambient air from entering interior portions of the battery through the porous pathways of the cathode. For example, the barrier layer may seal each of the macroporous pathways and the corresponding pores by at least partially covering the exterior surface of the cathode. The battery may be activated when the barrier layer is removed from the exterior surface of the cathode. For example, removal of the barrier layer from the exterior surface of the cathode may allow the ambient air to enter the cathode through the porous pathways and disperse throughout interior portions of the battery.

Another innovative aspect of the subject matter described in this disclosure can be implemented as a battery including a body defined by a metal anode and an cathode. The battery may also include a first separator layer disposed on the metal anode, a second separator layer disposed on the cathode, and a plurality of beads disposed within the body. The first and second separator layers may be or provide structural supports of the battery. In some aspects, the first and second separator layers may include a cellulose material infused with hydroxyl (OH—) ions. The plurality of beads may confine a liquid electrolyte, and may release the liquid electrolyte into interior portions of the battery in response to a compression of the cathode into the body of the battery. In some aspects, the beads may migrate within the body in response to exposure of the beads to an electric field. The migration of at least some of the beads may distribute the liquid electrolyte throughout the interior of the body of the battery. In some instances, the beads may remain in a dormant state in an absence of the compression of the cathode into the body of the battery. In some other instances, the beads may rupture in response to the compression of the cathode into the body of the battery. In one implementation, the body may include an adhesive layer having a thickness greater than or equal to a diameter of a respective bead.

The cathode may include a carbon-based textured scaffold having a plurality of catalytic sites. The catalytic sites may be configured to participate in one or more of an oxidation chemical reaction or a reduction chemical reaction. In some instances, the catalytic sites may be doped with manganese, manganese oxide (MnO), and platinum. In one implementation, the carbon-based textured scaffold has a surface area greater than approximately 1,000 m²/g.

In various implementations, the carbon-based textured scaffold may be a graded three-dimensional (3D) mesoporous-to-microporous open channeled graphene structure. In some implementations, the carbon-based textured scaffold may include an outer region and an inner region. The outer region may include a plurality of macroporous pathways configured to distribute oxygen and water vapor supplied by ambient air throughout the cathode and into interior portions of the body. The inner region may include a plurality of mesoporous pathways interconnected with the plurality of macroporous pathways and configured to drain an excess quantity of the water vapor from the cathode. The mesoporous pathways may be defined by a plurality of N-doped graphene particles fused together.

Details of implementations of the subject matter described in this disclosure are set forth in the accompanying drawings and the description below. Other features, aspects, and advantages will become apparent from the description, the drawings, and the claims. In the following figures, the relative dimensions of the drawings, diagrams, illustrations, and/or depictions may not be drawn to scale.

BRIEF DESCRIPTION OF THE DRAWINGS

Like reference numbers and designations in the various drawings indicate like elements.

DETAILED DESCRIPTION

Figure 1:
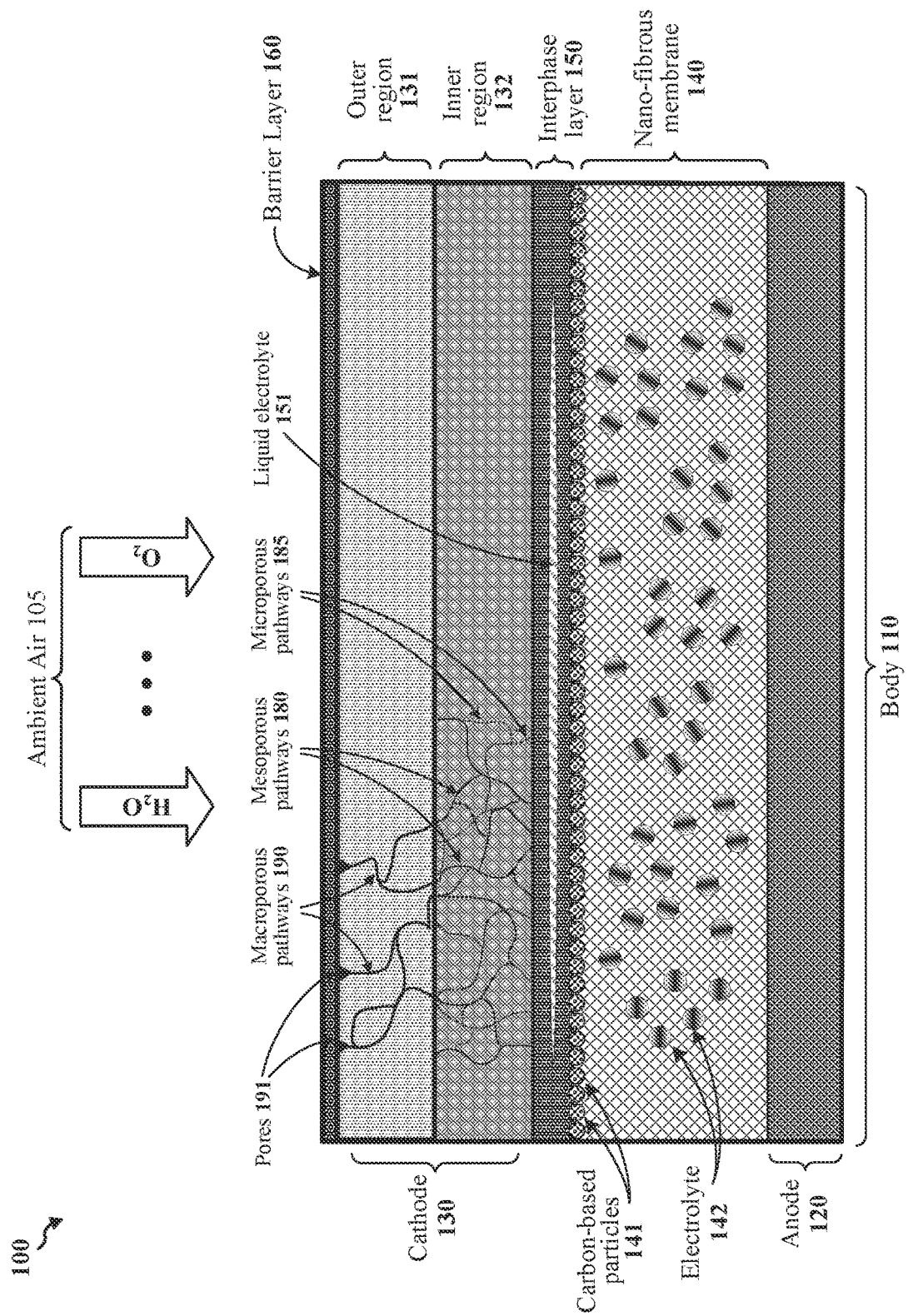
FIG. 1 shows a metal air battery, according to some implementations.

Various aspects of the present disclosure are provided in the following description and related drawings directed to various examples provided for illustration purposes. However, persons of ordinary skill in the art will readily recognize that the teachings herein can be applied in a multitude of different ways. The described implementations can be implemented in any air battery. Alternate aspects may be devised without departing from the scope of the disclosure. Additionally, well-known elements of the disclosure will not be described in detail or will be omitted so as not to obscure the relevant details of the disclosure.

A metal air battery such as a Zinc air battery typically includes an air cathode, a zinc anode, and a body containing an electrolyte. An air opening in the air cathode allows ambient air to flow into the battery. Chemical reactions between the ambient air and various materials within the metal air battery allow the battery to operate. For example, water vapor and oxygen supplied by the ambient air react at the air cathode to produce hydroxyl ions, which migrate through the electrolyte towards the zinc anode. Water vapor supplied by the ambient air can also be used to produce the electrolyte. The ions react with a mass of zinc at the anode to generate free electrons and zincate. The free electrons carry charge between the zinc anode and the air cathode, which in turn generates an output current and/or an output voltage that can be used to power a load.

One major drawback of metal air batteries is the inability to control the amount of water vapor that accumulates at or in the air cathode during the battery's discharge cycle. For example, because water vapor and oxygen present in the ambient air flow through the air cathode to reach interior portions of the battery (e.g., the electrolyte and exposed surfaces of the metal anode), water vapor accumulates in the air cathode. Moreover, chemical reactions associated with the discharge cycle of the metal air battery also produce water vapor at the air cathode, which may further increase the amount of water vapor accumulated in the air cathode. Excessive amounts of water vapor accumulated at or within the air cathode may degrade performance of the metal air battery. In some instances, the accumulated water vapor can flood the air cathode and, in some instances, may flood the air cathode, which in turn may damage not only the air cathode but also the metal anode. As such, there is a need to control the amount of water vapor accumulated in the cathode of a metal air battery during battery discharge operations.

In accordance with various aspects of the present disclosure, a metal air battery is disclosed that provides a mechanism through which the amount of water vapor accumulated in the cathode can be controlled. In various implementations, the cathode of a metal air battery may include a carbon-based textured scaffold that defines an open-channel network of interconnected porous pathways that can not only distribute ambient air throughout the cathode and interior portions of the battery to activate the battery, but that can also divert excess amounts of water vapor accumulated in the cathode for the production of electrolytes in the battery. In this way, implementations of the subject matter disclosed herein can prevent excessive amounts of water vapor supplied by the ambient air from flooding the cathode (and other portions of the battery). In addition, by diverting excess water vapor drained from the cathode for the production of electrolytes, batteries operating in accordance with the teachings disclosed herein may increase the rate and/or amount of electrolyte produced during battery discharge cycles (such as compared with conventional metal air batteries).

In some implementations, the metal air battery may include a barrier layer that can be removably disposed over an exterior surface of the cathode, for example, to maintain the battery in a dormant state prior to use. Specifically, when the battery is in the dormant state (such as in a warehouse or on a store shelf prior to purchase and activation by a user), the barrier layer can prevent ambient air from entering the cathode or interior portions of the battery via the open-channeled porous network by sealing the pores that lead to the porous pathways. In some instances, the battery can be activated by removing the barrier layer from the exterior surface of the cathode to expose the pores to ambient air in the external environment. When exposed, the pores allow the ambient air to enter the porous pathways of the cathode and thereafter disperse throughout the cathode and interior portions of the battery. Oxygen and water vapor supplied by the ambient air may react with each other at or in the cathode to start a series of chemical reactions that activate operation of the battery. In this way, the removable barrier layer may prevent inadvertent activation of the battery while in the dormant state, thereby increasing the shelf-life of batteries disclosed herein (as compared to conventional metal air batteries). These and other aspects of the present implementations are described in more detail below.

FIG. 1 shows a metal air battery 100, according to some implementations. The metal air battery 100 can be of any suitable shape, and may have any suitable physical dimensions or attributes. In some implementations, the metal air battery 100 may be configured to power one or more smart labels attached to a package or container. For example, in some instances, individual components of the metal air battery 100 may be printed (e.g., using a 3D printer) onto the package, container, or vessel and then compressed against one another to enclose the metal air battery. The enclosed metal air battery may provide power to one or more smart labels printed on the package or container. In other instances, the metal air battery 100 may be integrated within at least a portion of the one or more smart labels, for example, so that the metal air battery 100 can be printed onto the package or container in tandem with the one or more smart labels.

The metal air battery 100 is shown to include a body 110, an anode 120, a cathode 130, a nano-fibrous membrane (NFM) 140, a hygroscopic interphase layer 150, and a barrier layer 160. The body 110 may be defined by the anode 120 and the cathode 130, and may contain an electrolyte 142. The anode 120 may be disposed on or within a first surface of the body 110, and may include any suitable type of metal such as (but not limited to) magnesium, zinc, or aluminum. In some aspects, the anode 120 may be formed as a thin metal film over one or more portions of the NFM 140, and may be at least partially evaporated under vacuum conditions. The cathode 130 may be formed on or within a second surface of the body 110 opposite the first surface. The cathode 130 may include a carbon-based textured scaffold (not shown in FIG. 1 for simplicity) that includes a plurality of porous pathways through which ambient air 105 can be distributed throughout the cathode 130 and into interior portions of the battery 100. The textured scaffold may be deposited, plated, or grown on one or more exposed surfaces of the cathode 130 in any suitable manner. In some aspects, the textured scaffold includes a plurality of catalytic sites that can participate in chemical oxidation reactions when the battery 100 is activated. The catalytic sites may be doped with manganese, manganese oxide (MnO), and platinum. In one implementation, the carbon-based textured scaffold has a surface area greater than approximately 1,000 $m^2/g$.

The NFM 140 may be disposed between the anode 120 and the cathode 130. The NFM 140 may be coated with a layer of carbon-based particles 141 such as (but not limited to) sp3 diamond-like carbons or sp2 graphene layers and/or nanoplatelets. In some instances, the coating of carbon-based particles 141 may be deposited on the NFM 140 using a non-thermal microwave plasma torch, for example, as described in commonly owned U.S. Pat. No. 9,767,992, the entirety of which is incorporated by reference herein. The NFM 140 may be pre-loaded with dry salts and hygroscopic agents. The dry salts may produce a liquid electrolyte 142 when exposed to or hydrated by water vapor. The hygroscopic agents may absorb water vapor supplied by the ambient air 105 and hydrate the dry salts with the water vapor, which may increase the rate at which the dry salts can produce the liquid electrolyte 142. In some instances, the dry salts may include one or both of sodium hydroxide (NaOH) or potassium hydroxide (KOH), and the hygroscopic agents may include one or more of glycerin/glycerol ($C_3H_8O_3$), ethanol ($C_2H_5OH$), methanol ($CH_3OH$), concentrated sulfuric acid ($H_2SO_4$), or concentrated sodium hydroxide (NaOH). In other instances, other suitable salts and/or hygroscopic agents may be used.

In some implementations, the NFM 140 may be a metal organic framework (MOF) including poly(vinyl alcohol) (PVA), polyamide (PA), micro-crystalline cellulose (MCC), or any combination thereof. In other implementations, the NFM 140 may be formed from naturally occurring or naturally derived substances such as Chitosan. Chitosan is a linear polysaccharide composed of randomly distributed β-linked D-glucosamine and N-acetyl-D-glucosamine. Chitosan can be made by treating the chitin shells of shrimp and other crustaceans with an alkaline substance, such as sodium hydroxide (NaOH). In some other implementations, the NFM 140 may be based on carboxymethyl cellulose (CMC), which may be used with any organic electrolyte. CMC, which is also known as "cellulose gum," is a cellulose derivative with carboxymethyl groups bound to some of the hydroxyl groups of the glucopyranose monomers that make up the cellulose backbone. In some instances, CMC may be used as its sodium salt, otherwise known as sodium carboxymethyl cellulose. In some aspects, the NFM 140 made from Chitosan and/or CMC may be configured to operate in conjunction with a current collector (such as a copper current collector) in metal air batteries such as (but not limited to) the metal air battery 100.

The hygroscopic interphase layer 150 may be disposed between the cathode 130 and the NFM 140. The interphase layer 150 may include a liquid electrolyte 151 such as, for example, the electrolyte 142 produced by the NFM 140 when exposed to or hydrated by water vapor. In some implementations, the interphase layer 150 may be used to drain excess water vapor from the cathode 130 and/or to hydrate the salts contained in the NFM 140. In some instances, the interphase layer 150 may include a plurality of microporous pathways that can drain excess quantities of water vapor accumulated at or in the cathode to prevent the water vapor supplied by the ambient air 105 from flooding the cathode 130 and/or other portions of the battery 100. Specifically, the microporous pathways of the interphase layer 150 may direct water vapor from the cathode 130 to the NFM 140. The water vapor from the cathode 130 may provide additional hydration of the salts contained in the NFM 140, which in turn may increase production of the electrolyte 142 in the NFM 140. The increased production of electrolyte 142 may improve performance of the battery 100, for example, by increasing the specific capacity of the battery 100.

The barrier layer 160 may be removably disposed over all or a portion of an exterior surface of the cathode 130, for example, to maintain the battery 100 in a dormant state prior to use. For example, when the battery 100 is in a dormant state (such as in a warehouse or on a store shelf prior to purchase and activation by a user), the barrier layer 160 can prevent ambient air 105 from entering the cathode 130 or interior portions of the battery 100 via the open-channeled porous network by sealing the pores 191 formed within the exterior surface of the cathode 130. In this way, the removable barrier layer 160 may prevent inadvertent activation of the battery 100 while in the dormant state, thereby increasing the shelf-life of the battery 100 as compared to conventional metal air batteries.

The battery 100 can be activated by removing the barrier layer 160 from the exterior surface of the cathode 130 such that the pores 191 are exposed to the external environment. For example, a user may activate the battery 100 by peeling the barrier layer 160 from the exterior surface of the cathode 130 so that the ambient air 105 can enter the porous pathways 180 and 190 of the cathode 130 through the exposed pores 191. Oxygen and water vapor supplied by the ambient air 105 may react with each other at or in the cathode 130 to start a series of chemical reactions that activate operation of the battery 100.

In some instances, the porous pathways 180 and 190 can direct oxygen and water vapor supplied by the ambient air 105 throughout the cathode 130 and into the NFM 140. The water vapor may hydrate the salts contained in the NFM 140 to produce the liquid electrolyte 142. The hygroscopic agents contained in the NFM 140 may absorb some of the water vapor and further hydrate the salts. Once produced, the electrolyte 142 disperses throughout the NFM 140 and provides a mechanism for transporting ions and/or electrons between the anode 120 and the cathode 130. Oxygen and water vapor supplied by the ambient air 105 react at the cathode 130 to produce hydroxyl ions, which migrate through the liquid electrolyte 142 towards the metal anode 129. A mass of metal (such as Zinc) supplied by the anode 120 reacts with the hydroxyl ions to produce zincate and free electrons. Migration of the hydroxyl ions through the liquid electrolyte 142 may release electrons (other free electrons) from the electrolyte 142. The resulting quantity of free electrons may carry charge, and thus a current, between the anode 120 and cathode 130 of the battery. Since both the water vapor and oxygen necessary for operation of the battery 100 can be supplied by the ambient air 105, there is a potentially unlimited supply of fuel for the battery 100.

As discussed, porous pathways formed within the textured scaffold of the cathode 130 can be used to distribute the water vapor, gaseous oxygen, and other components of the ambient air 105 throughout the cathode 130 and into interior portions of the metal air battery 100. In some implementations, the textured scaffold may include an outer region 131 and an inner region 132. In some instances, macroporous pathways 190 may be formed or defined within the outer region 131 of the cathode, and mesoporous pathways 180 may be formed or defined within the inner region 132 of the cathode. The macroporous pathways 190 can distribute oxygen and water vapor supplied by the ambient air 105 throughout the cathode 130 and into interior portions of the body 110 (such as the NFM 140). The mesoporous pathways 180 may be interconnected with the macroporous pathways 190, and can drain excess water vapor from the cathode 130 and/or direct water vapor from the cathode 130 to the NFM 140. In some instances, the mesoporous pathways 180 may be defined by a plurality of N-doped graphene particles fused together. In some implementations, the macroporous pathways 190 have a diameter greater than approximately 50 nanometers, and the mesoporous pathways 180 have a diameter between approximately 2 and 30 nanometers. In various implementations, the inner region 132 of the cathode 130 may also include a plurality of microporous pathways e 185 connected to the mesoporous pathways 180 and interconnected with the macroporous pathways 190. In some aspects, the inner region 132 may have a thickness between approximately 0.1 and 50 microns, the outer region 131 may have a thickness between approximately 10 and 50 microns, and the hygroscopic interphase layer 150 may have a thickness between approximately 2 and 10 nanometers.

In some implementations, the carbon-based textured scaffold of the cathode 130 may be a graded three-dimensional (3D) open channeled graphene structure having macroporous pathways 190, mesoporous pathways 180, and microporous pathways 185. For example, the 3D open channeled graphene structure may include microporous pathways 185 and mesoporous pathways 180 defined in the inner region 132 of the cathode 130, and may include macroporous pathways 190 defined in the outer region 131 of the cathode 130. In some instances, the microporous pathways 185 may include a plurality of N-doped graphene particles fused together at one or more angles. In addition, or in the alternative, the microporous pathways 185 and the mesoporous pathways 180 may include inward-facing bi-modal interfaces. As discussed, the macroporous pathways 190 can be used to distribute water vapor and oxygen supplied by the ambient air 105 throughout the cathode 130, and the mesoporous pathways 180 can be used to drain excess water vapor from the cathode 130 towards the NFM 140. In this way, the 3D open channeled graphene structure of the cathode 130 may not only remove excess water vapor from the cathode 130 but may also hydrate the salts contained in the NFM 140, thereby increasing the rate at which the salts contained in the NFM 140 can be converted into the liquid electrolyte 142 while also managing water content in the cathode 130.

During operation of the metal air battery 100, oxygen reduction reactions (ORR) involving stable platinum (Pt) based electrocatalysts and/or carbon materials may occur at the cathode 130 while metal oxidation occurs at or near the metal anode 120. In one implementation, the metal air battery 100 may operate based on one or more of the following equations:

$$\text{anode: } Zn+4OH^- \rightarrow Zn(OH)_4^{2-}+2e^- (E_0=-1.25V) \quad \text{(Eq. 1)}$$

$$\text{electrolyte: } Zn(OH)_4^{2-} \rightarrow ZnO+H_2O+2OH^- \quad \text{(Eq. 2)}$$

$$\text{cathode: } \tfrac{1}{2}O_2+H_2O+2e^- 2OH^- (E_0=0.34V\ pH=11) \quad \text{(Eq. 3)}$$

$$\text{entire battery: } 2Zn+O_2 \rightarrow 2ZnO (E_0=1.59V) \quad \text{(Eq. 4)}$$

In various implementations, the metal air battery 100 may have an energy density between approximately 1,480 Wh/L and 9,780 Wh/L, an approximate specific power of 100 W/kg, and an approximate nominal cell voltage of 1.65 V. In some instances, the metal air battery 100 may be a non-rechargeable or primary battery (e.g., a "primary" battery). In other instances, the metal air battery 100 may be a rechargeable battery (e.g., a "secondary" battery).

The metal air battery 100 may have a relatively high energy density and specific energy ratio compared to other types of batteries, for example, because the metal air battery 100 can be powered by one or more reactants typically present in the ambient air 105. That is, rather than relying on materials loaded into the body 110 of the battery 100 as a fuel source, the metal air battery 100 can use the ambient air 105 as a fuel source. In this way, the metal air battery 100 may have more of its internal volume available for holding or storing electrolytes 142 than similar-sized conventional batteries, which may allow the metal air battery 100 to achieve higher energy densities and specific energy ratios than similar-sized conventional batteries. For example, in one example implementation for which the body 110 has a lateral dimension (e.g., diameter) of approximately 11.6 mm and a height of approximately 5.4 mm, the metal air battery 100 can have a specific capacity as high as 620 mAh. By way of example, conventional batteries of the same size typically have a specific capacity between approximately 150 mAh and 200 mAh.

The operating life of the metal air battery 100 may depend on its exposure to the ambient air 105. Specifically, the electrolytes 142 contained within the body 110 of the battery 100 may lose water more rapidly at higher temperatures and lower humidity than at lower temperatures and higher humidity. Moreover, since potassium hydroxide (KOH) tends to liquify in very humid conditions, inclusion of KOH in the electrolytes 142 may cause excess water to accumulate within the body 110, which in turn may flood various multi-porous channels or pathways within the cathode 130. Excess water may flood into these channels and degrade their ability to be functionalized with certain materials. In some implementations, KOH contained in the electrolyte 142 may also react with carbon dioxide ($CO_2$) present in the ambient air 105.

In various implementations, the cathode 130 can maintain its physical properties during discharge cycles. Accordingly, the terminal voltage of the metal air battery 100 may be stable until exhaustion. In some aspects, the power capacity of the metal air battery 100 may depend on several variables including (but not limited to) catalytic values of exposed surface areas of the cathode 130, internal porosity of the cathode 130, availability of ambient air 105, and concentration levels of various components of the ambient air 105. The rate at which gaseous oxygen present in the ambient air 105 enters interior portions of the metal air battery 100 through the air opening 180 may be balanced against water loss from the electrolyte 142 and/or the cathode 130. As such, in some implementations, the metal air battery 100 may be configured such that the cathode 130 includes membranes and/or pathways coated with a hydrophobic material to control and/or limit water loss. In one implementation, the air opening 180 may include a plurality of openings or air holes extending from an exterior of the body 110 into interior portions of the body 110 so that water vapor and oxygen present in the ambient air 105 can activate the metal air battery 100 by entering interior portions of the metal air battery 100. Specifically, the water vapor may react with dry salts loaded within the NFM 140 to produce a liquid electrolyte that can carry ions from the cathode 130 to the metal anode 120, and the oxygen may react with metal (such as Zinc) within the metal anode 120 to release electrons that can carry charge between the cathode 130 and the metal anode.

When the metal air battery 100 is deployed in environments having relatively low humidity (such as lower than 30% humidity), the metal air battery 100 may experience greater water loss from the electrolyte 142. In some instances, the metal air battery 100 may fail when water loss becomes greater than approximately 80%. Also, when the temperature of the environment decreases below approximately 68° F., the storage capacity of the metal air battery 100 may decrease. In some instances, the discharge rate of the metal air battery 100 may degrade its capacity. For example, while the metal air battery 100 may be able to deliver up to 80% of its total storage capacity when discharged over a relatively long period of time (such as 300 hours) at a given temperature, the metal air battery 100 may be able to deliver only 80% of its total storage capacity when discharged over a relatively short period of time (such as 50 hours).

In some implementations, the catalytic sites of the textured scaffold associated with the cathode 130 may be doped with selected catalysts such as (but not limited to) manganese, manganese oxide (MnO), and platinum. These selected catalysts have higher catalytic activity and durability in concentrated alkaline electrolytes than traditional precious metal platinum (Pt) and iridium (Ir) catalysts. In some aspects, cobalt (II) oxide (CoO) and/or as nickel-iron (Ni—Fe) layered double hydroxide oxygen evolution catalysts may be provided in the electrolyte 142. For example, when the cathode 130 is doped with CoO and/or Ni—Fe catalysts, the metal air battery 100 may have a peak power density of approximately 265 $mW/cm^3$, a peak current density of −200 $mA/cm^3$ at 1 V, and an energy density >700 Wh/kg. In other aspects, metal platinum (Pt) and iridium (Ir) catalysts may be used to dope the active sites of the multiple pathways and/or carbon nanotubes of the cathode 130. In some other aspects, the CoO, Ni—Fe, Pt, or Ir catalysts may be replaced by a carbon-based, metal-free electrocatalyst that can be incorporated within the cathode 130. These carbon-based, metal-free electrocatalysts may facilitate oxygen reduction reactions and oxygenation reactions within the metal air battery 100.

In some implementations, the cathode 130 may include an organic compound aniline polymerized into long chains in a phytic acid solution and freeze-dried into a stable, mesoporous carbon aerogel having pores of various sizes between approximately 2 and 50 nm. The mesoporous carbon aerogel may provide a relatively large surface area that allows the electrolyte 142 to diffuse into interior portions of the body 110 of the metal air battery 100. In some aspects, the mesoporous carbon aerogel may be pyrolyzed to approximately 1,000° C. to turn the mesoporous carbon aerogel into a graphitic and/or an organized graphene network having many catalytic graphene edges. The aniline may dope the mesoporous carbon aerogel with nitrogen, which may further facilitate the oxygen reduction reactions and oxygenation reactions within the metal air battery 100.

In some aspects, the mesoporous carbon aerogel may be infused with phosphorus (P) via phytic acid, which may increase oxygen evolution associated with the battery and thereby increase the specific capacity of the metal air battery 100. In some implementations, the mesoporous carbon aerogel may have a surface area of approximately 1,663 $m^2/gr$. In implementations for which the cathode 130 includes a graphitic and/or organized graphene network, the metal air battery 100 may provide an open-circuit potential of 1.48 volts, a specific capacity of 735 mAh/gr (Zn), an energy density of 835 Wh/kg (Zn), and/or a peak power density of 55 $mW/cm^3$. In some aspects, the textured scaffold of the cathode 130 may be doped with nitrogen (N) to create hierarchical nitrogen (N)-doped porous carbons (NPCs). The NPCs may be synthesized by ball milling, followed by pyrolysis.

As discussed, the cathode 130 may include a graded 3D mesoporous-to-microporous open channeled graphene structure including microporous pathways 185 and mesoporous pathways 180 configured such that the microporous pathways J can lead water vapor into the cathode 130 and the mesoporous pathways 185 can drain excess water vapor from the cathode 130. In some instances, the open channeled graphene structure may be N-doped along basal planes of the carbon structures, for example, to increase oxygen reduction associated with the water vapor and/or gaseous oxygen provided by the ambient air 105. Also, N-doping the graphene structure may create hydrophobic surfaces that can diffuse water vapor and gaseous oxygen throughout the NFM 140. As such, in some implementations, the cathode 130 may include 3D hierarchical mesoporous-to-microporous pathways with exposed functionalized surfaces for oxygen transport and reduction. In addition, or the alternative, the cathode 130 may passively transport water vapor to the interphase layer 150 during activation and/or hydration of the NFM 140, for example, to increase the rate at which dry salts loaded into the NFM 140 are hydrated with water vapor to produce a liquid electrolyte suitable for transporting ions from the cathode 130 to the metal anode 120.

Figure 2:
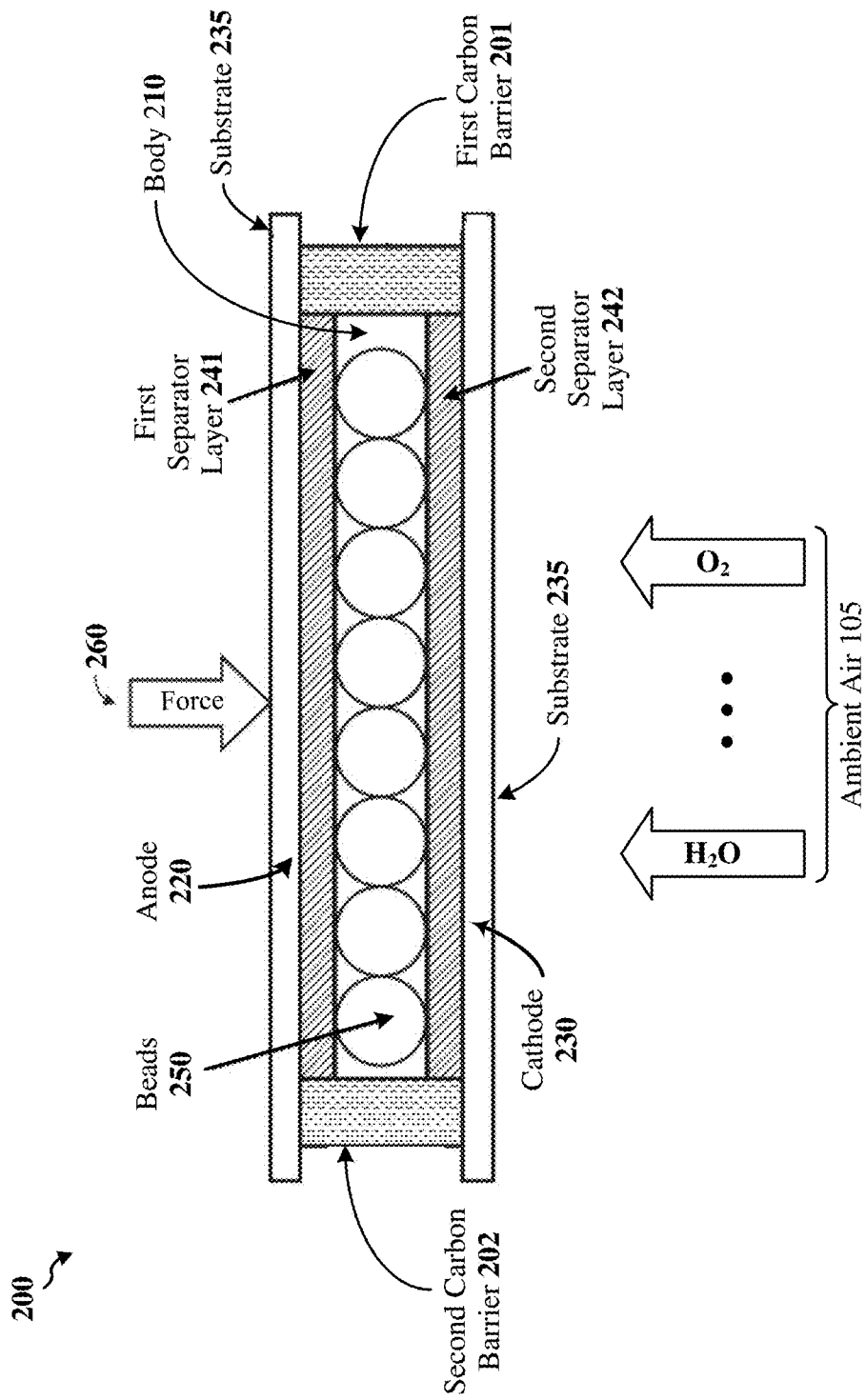
FIG. 2 shows a battery, according to other implementations.

FIG. 2 shows an air battery 200, according to other implementations. The air battery 200 is shown to include a body 210 defined by a metal anode 220 and an cathode 230. The battery 200 may also include a first separator layer 241 disposed on the metal anode 220, a second separator layer 242 disposed on the cathode 230, and a plurality of beads 250 disposed within the body 210. The first and second separator layers 241 and 242 may provide structural support for the battery 200. In some aspects, each of the first and second separator layers 241 and 242 may include a cellulose material infused with hydroxyl (OH⁻) ions.

The plurality of beads 250 may collectively hold or store an amount or volume of liquid electrolyte (not shown for simplicity). In some implementations, each of the beads 250 may include a polymeric shell, and may be configured to release the liquid electrolyte into one or more interior portions of the battery 200 in response to an external force applied to the battery 200. Specifically, when a force 260 applied to the metal anode 220 exceeds a threshold value, the metal anode 220 may be compressed into interior portions of the body 210 with sufficient force to squeeze, crush, tear, and/or rupture the beads 250 such that the liquid electrolyte is released from the ruptured beads 250. In this way, a user can activate the battery 200 by compressing or squeezing the body 110 of the battery with enough force to squeeze, crush, tear, and/or rupture the beads 250 such that the liquid electrolyte is released from the beads 250 into interior portions of the body 210. Once released from the beads 250, the liquid electrolyte may be available to participate in chemical reactions associated with operating the battery 200 (e.g., to transport ions from the cathode 230 to the anode 220 and/or release electrons that can carry charge between the battery's electrodes.

In some implementations, the plurality of beads 250 may also be configured to electrophoretically migrate within the interior portions of the body 210 in the presence of an electric field applied between the metal anode 220 and the cathode 230. For example, prior to activating the battery 200, the user can cause the beads to migrate within the interior portions of the battery 200 by applying the electric field between the metal anode 220 and the cathode 230. The resulting migration of the beads 250 within the interior portions of the battery 200 may increase the speed and extend to which the liquid electrolyte is distributed throughout the interior portions of the battery 200. In this way, the user may increase the specific capacity of the battery 200. In some instances, the body 210 may include an adhesive layer (not shown for simplicity) having a thickness greater than or equal to a diameter of a respective deformable bead 250.

In various implementations, the cathode 230 may be or may include a carbon-based textured scaffold (not shown for simplicity) having a plurality of catalytic sites. The catalytic sites may be configured to participate in one or more of an oxidation chemical reaction or a reduction chemical reaction. In some instances, the catalytic sites may be doped with manganese, manganese oxide (MnO), and platinum. In some implementations, the textured scaffold may define a porous network including hydrophilic diffusional pathways and hydrophobic diffusional pathways that can be used to distribute water vapor, gaseous oxygen, and other components of the ambient air 105 throughout the cathode 230. In some instances, the hydrophilic diffusional pathways and the hydrophobic diffusional pathways may be doped with one or more materials that can increase oxygen reduction in the battery 200. In some aspects, the textured scaffold has a surface area greater than approximately 1,000 m²/g.

In other implementations, the textured scaffold of the cathode 230 may include a plurality of first channels configured to distribute water vapor and oxygen in the ambient air throughout the cathode, and a plurality of second channels configured to pump excess water vapor from the cathode 230. The first and second channels may be functionalized with one or more additives. The first channels may have a dimension between approximately 0.5 and 20 microns, and the second channels may have a dimension between approximately 0.5 and 1 micron. In some other implementations, the textured scaffold of the cathode 230 may include a graded 3D mesoporous-to-microporous open channeled graphene structure. Specifically, the open channeled graphene structure may include microporous pathways defined in an inner portion of the cathode 230 that can lead water vapor into the cathode 230, and mesoporous pathways defined in an outer portion of the cathode 230 that can drain excess water vapor from the cathode 230. In some instances, the microporous pathways are defined by a plurality of N-doped graphene particles fused together at one or more angle. The open channeled graphene structure may also include a plurality of macroporous pathways that can drain excess water vapor from the cathode 230. In some instances, the macroporous pathways may have a diameter greater than 50 nanometers, the mesoporous pathways may have a diameter between approximately 20 and 50 nanometers, and the microporous pathways may have a diameter less than 2 nanometers.

In some implementations, the battery 200 may be a multi-part battery that remains in a dormant state until assembled and activated. For example, in some instances, a user can assemble and activate the battery 200 by positioning the metal anode 220 and the cathode 230 over each other in a vertical alignment, and then folding the metal anode 220 and the cathode 230 towards each other until interior portions of the battery 200 are sealed from the external environment. In other implementations, the cathode 230 and/or the metal anode 220 may be 3D printed onto thin flexible substrates in a sandwich-type configuration that can hold beads 250 containing the liquid electrolyte.

Figure 3:
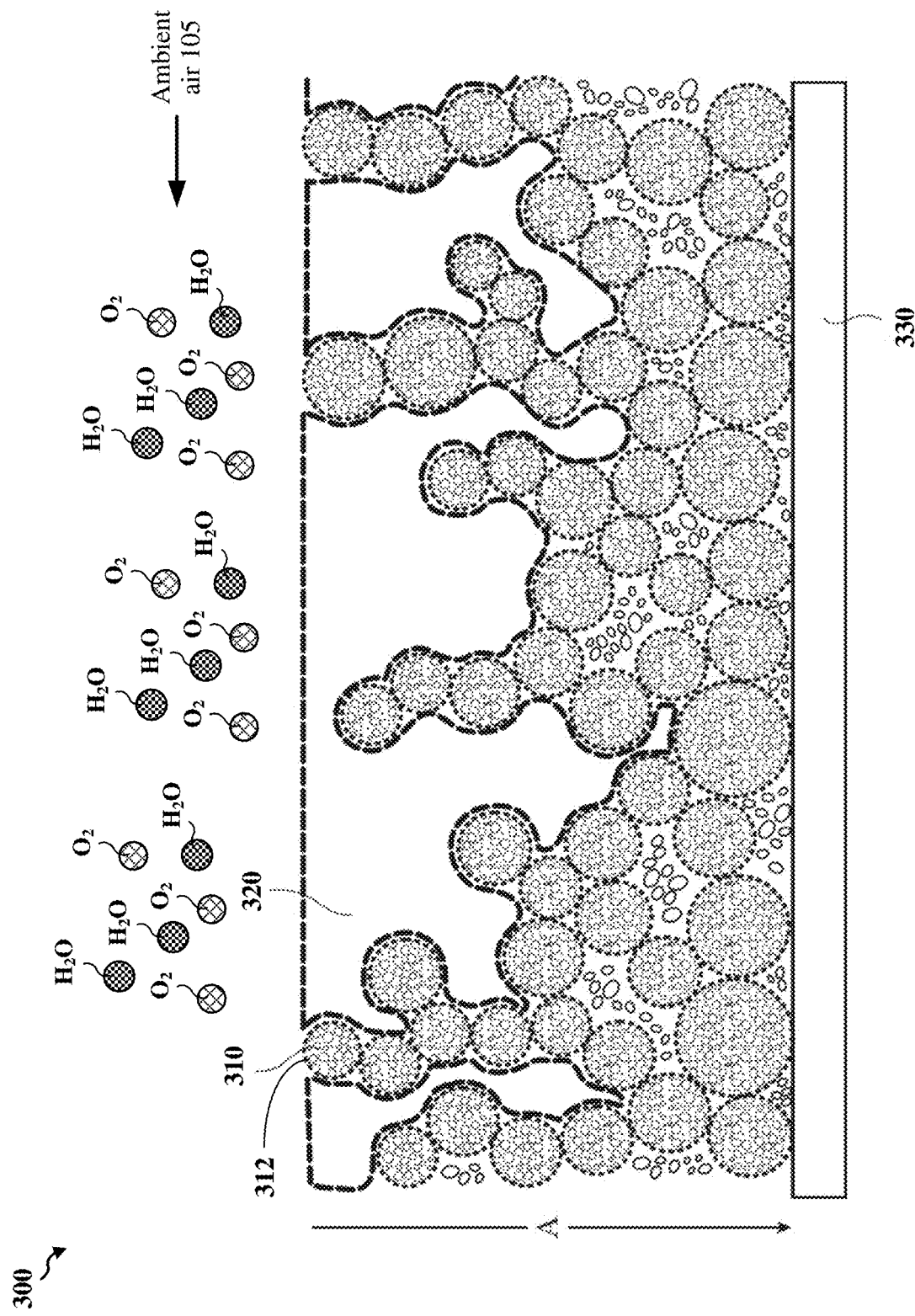
FIG. 3 shows a schematic diagram depicting a carbon-based structure that may be used in an cathode of a battery, according to some implementations.

FIG. 3 shows a schematic diagram depicting a carbon-based structure 300 that may be used in an cathode of a battery, according to some implementations. In some implementations, the carbon-based structure 300 may be used as the carbon-based textured scaffold to form the cathode 130 of the metal air battery 100 of FIG. 1 and/or the cathode 230 of the air battery 200 of FIG. 2. As shown, the carbon-based structure 300 may include a plurality of carbon-based particles 310 and an interface region 320 deposited onto a current collector 330. The interface region 320 may be exposed to ambient air 105, for example, so that water vapor, gaseous oxygen, and other components present in the ambient air 105 can permeate throughout the interface region 320 and into the carbon-based particles 310.

In some implementations, the carbon-based particles 310 can be formed by flowing a vapor flow stream of carbon-containing species (such as methane (CH₄) into a chemical reactor, and cracking the carbon-containing species to produce a high-quality elemental carbon. In some instances, the chemical reactor may be a thermal reactor or a microwave-based reactor that can yield high-quality elemental carbon without carbon monoxide contamination and with virtually no carbon dioxide emissions, for example, as described in commonly-owned U.S. Pat. No. 9,767,992 entitled "MICROWAVE CHEMICAL PROCESSING REACTOR," which is incorporated by reference herein. A basic endothermic reaction that may occur within a microwave reactor to create the carbon-based particles 310 is shown as equation (5) below:

$$CH_4 + 74.85 kJ/mol \rightarrow C + 2H_2 \qquad (5)$$

Carbon derived from hydrocarbon cracking processes may fuse together while being dispersed in a gaseous phase, referred to as in-flight, to create the carbon-based particles 310, which may form the carbon-based structure 300. In some implementations, fusion of carbon-containing radical species during synthesis and/or manufacture of the carbon-based structure 300 may define interconnections between the carbon-based particles 310. In some instances, one or more groups of carbon-based particles 310 can collectively form a carbon-based agglomeration 312. Each of the agglomerations 312 may include single layer graphene (SLG), few layer graphene (FLG) having between 5 and 15 layers of graphene, or many layer graphene (MLG) having more than 15 layers of graphene. In some aspects, the graphene layers or structures are fused together to conduct electricity along and across contact points of the graphene layers. The microstructures and/or pathways defined within and between one or more agglomerations 312 can be used to transport ions between the cathode and anode of a metal air battery such as (but not limited to) the battery 100 of FIG. 1 or the battery 200 of FIG. 2.

In some implementations, the agglomerations 312 may collectively define a plurality of first channels configured to distribute water vapor and oxygen in the ambient air throughout the cathode of a metal air battery, and a plurality of second channels configured to pump excess water vapor from the cathode of the metal air battery. In some instances, the first and second channels may be functionalized with one or more additives. The first channels may have a dimension between approximately 0.5 and 20 microns, and the second channels may have a dimension between approximately 0.5 and 1 micron.

In other implementations, the agglomerations 312 may collectively define a plurality of microporous pathways formed in inners portion of the cathode, and a plurality of mesoporous pathways formed in outer portions of the cathode. The microporous pathways may be used to direct water vapor supplied by the ambient air 105 into the cathode, and the mesoporous pathways may be used to drain excess water vapor from the cathode. In some aspects, the microporous pathways be defined by a plurality of N-doped graphene particles fused together at one or more angles. In one implementation, the agglomerations 312 may also collectively define a plurality of macroporous pathways that can be used to drain excess water vapor from the cathode. In some instances, the macroporous pathways have a diameter greater than 50 nanometers, the mesoporous pathways have a diameter between approximately 20 and 50 nanometers, and the microporous pathways have a diameter less than 2 nanometers.

In some instances, the agglomerations 312 may be orthogonally fused together in-flight without using a separate binder material, as commonly found in conventional systems. Orthogonal fusing is different from sintering (which compacts and forms a solid mass of material by heat or pressure such that materials are bonded at specific acute angles relative to one another). In some aspects, the electrical conductivity of the agglomerations 312 may be tuned by adding metal and/or one or more dopants during manufacturing of the metal air battery. Other manufacturing parameters can be adjusted to tune any number of properties or characteristics of the agglomerations 312 and/or the carbon-based particles 310. For example, an energy level of the carbon during formation of the agglomerations 312 may determine whether or not the carbon-based particles 310 will bond with each other. In some aspects, the carbon-based structure 300 can be grown in an atmospheric plasma-based vapor flow stream either in-flight or directly onto the current collector 330, which may increase the tunability of the carbon-particles 310.

In various implementations, the carbon-based particles 310, the carbon-based structure 300, and/or other carbon-based materials described herein can be manufactured via self-nucleation using a suitable chemical reactor (such as the chemical reactor described in commonly-owned U.S. Pat. No. 9,767,992). In one implementation, the carbon-based particles 310, the carbon-based structure 300, and/or other carbon-based materials described herein may have hydrophobic regions to inhibit wetting, may have hydrophilic regions to promote wetting, may have hygroscopic regions for the adsorption of water vapor during battery activation, may have nanoscopic active materials, or any combination thereof. In some implementations, the nanoscopic active materials may include (but are not limited to) $MnO_2$ or hydrogen) which may be incorporated directly onto/into the surface of nanostructured carbons.

Figure 4:
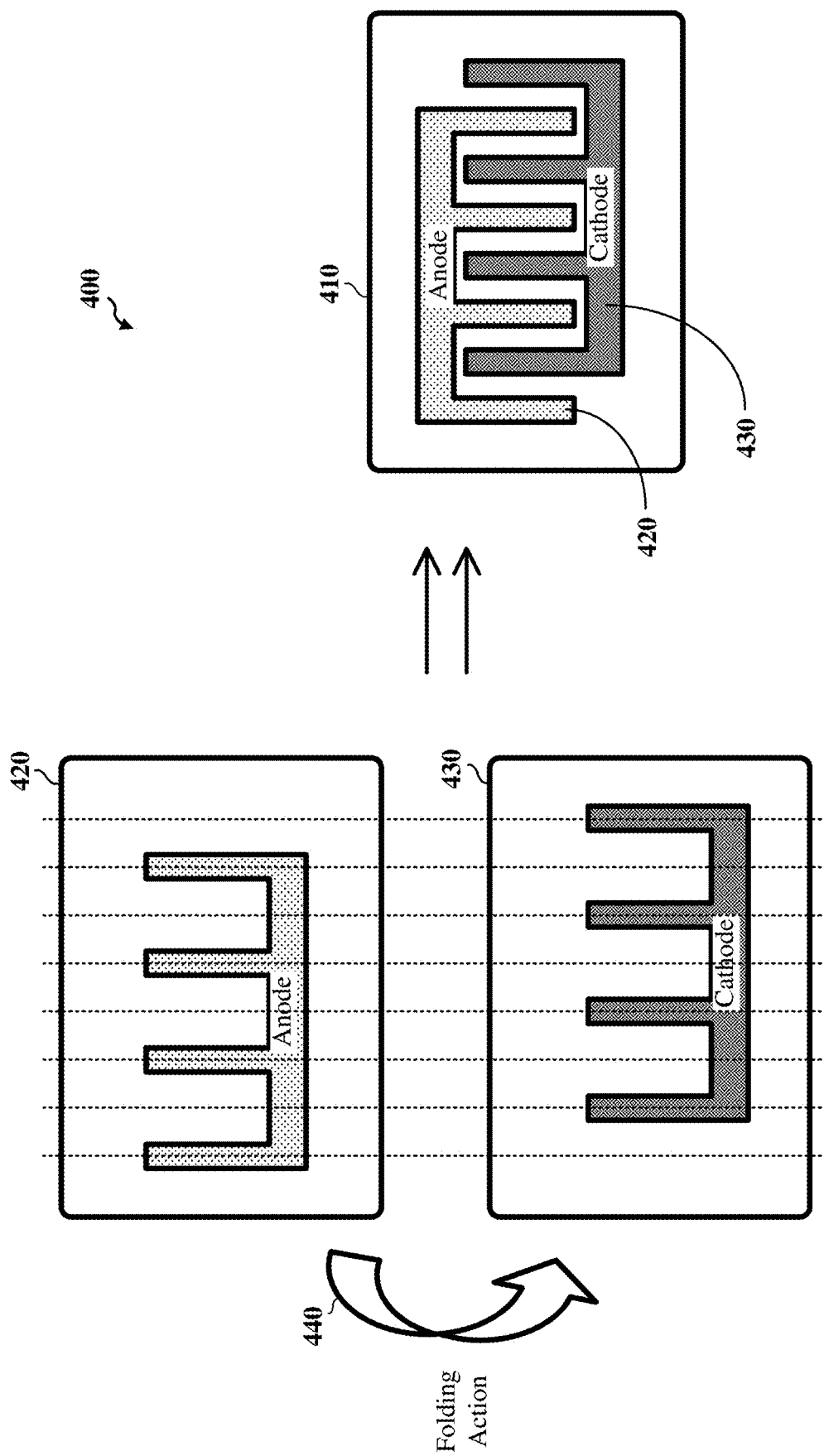
FIG. 4 is an illustration depicting assembly and activation of a battery, according to some implementations.

FIG. 4 is an illustration 400 depicting an example assembly and activation of a battery 410, according to some implementations. The battery 410, which may be one example of the battery 100 of FIG. 1 or the battery 200 of FIG. 2, is shown to include an anode 420 and a cathode 430 that can be formed as separate and distinct battery components. In some implementations, a user may position the anode 420 over the cathode 430, and then use a folding action 440 to fold the anode 420 towards the cathode 430 until the anode 420 and cathode 430 are compressed into each other to form the battery 410. As shown, the battery 410 has an interdigitated configuration in which one or more fingers of the anode 420 extend into the cathode 430, and one or more fingers of the cathode 430 extend into the anode 420. In some instances, the interdigitated configuration of the anode 420 and cathode 430 may allow the battery 410 to be activated once exposed to ambient air. The anode 420 may be any suitable anode such as (but not limited to) the metal anode 120 of FIG. 1 and/or the anode 220 of FIG. 2. The cathode 430 may be any suitable cathode such as (but not limited to) the cathode 130 of FIG. 1 and/or the cathode 230 of FIG. 2.

Figure 5:
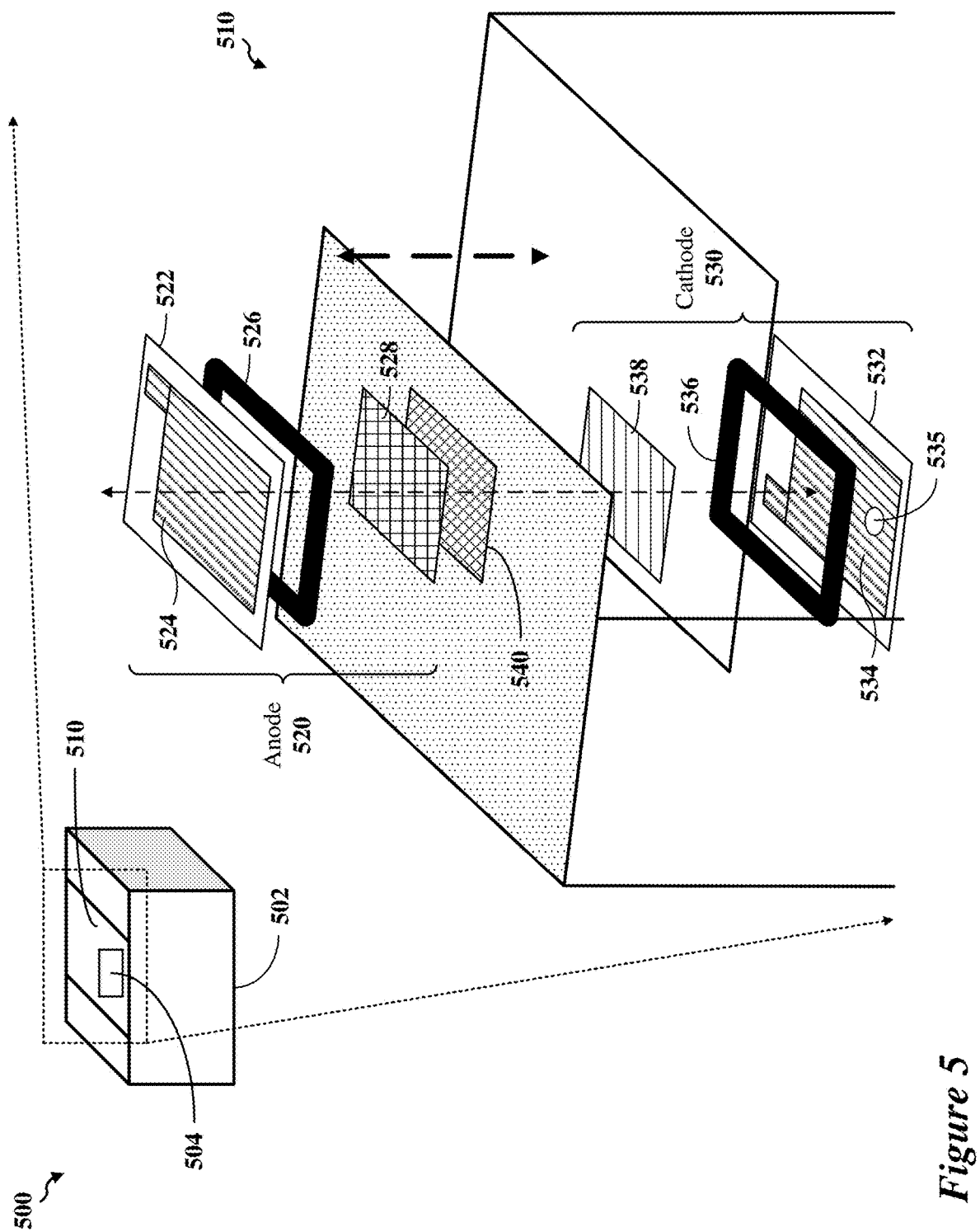
FIG. 5 is an illustration depicting assembly and activation of a battery, according to other implementations.

FIG. 5 is an illustration 500 depicting assembly and activation of a battery 510, according to other implementations. Although not shown in its entirety, the battery 510 includes an anode 520, an cathode 530, and an electrolyte mixture 540. In some implementations, the battery 510 may be used to power a smart label 504 affixed to a container 502. The container 502 may be any container, package, or box suitable for containing items to be shipped, delivered, or otherwise transported.

The anode 520 is shown to include a substrate 522, a current collector 524, a seal 526, and an electrode 528. The current collector 524 may be printed onto the substrate 522. The cathode 530 is shown to include a substrate 532, a current collector 534, a seal 536, and an electrode 538. An air opening 535 formed in the substrate 522 and current collector 524 allows ambient air to enter interior portions of the battery 510 and react with the electrolyte mixture 540 and exposed carbon surfaces of the cathode 530. In some aspects, the air opening 535 may be similar to the air opening 180 of FIG. 1.

The liquid electrolyte 540 may be or may include any electrolyte suitable for use with metal air batteries. In some instances, the liquid electrolyte may include potassium hydroxide (KOH) and/or sodium hydroxide (NaOH). The liquid electrolyte 540 may disperse uniformly throughout various pathways, conduits, and channels formed in or defined by the cathode 530. As such, the liquid electrolyte 540 may provide a polar medium through which ions may be readily transported and participate in the chemical reactions described with reference to FIG. 1. The seal 526 may seal various components of the anode 520 to prevent ambient air from flowing into interior portions of the anode 520, and to prevent ions and other chemicals, particle, or gases from leaking outside the anode 520. Similarly, the seal 536 may seal various components of the cathode 530 to prevent ambient air from flowing into interior portions of the cathode 530, and to prevent ions and other chemicals, particle, or gases from leaking outside the cathode 530.

In some instances, the battery 510 may be integrally formed within a surface of the container 502. In other instances, the battery 510 may be printed on a surface of the container 502. In some other instances, the battery 510 may be formed as part of the smart label 504. For example, the battery 510 may be printer label or format compatible with a variety of smart labels and offer a simple, reliable user-activated procedure. In this way, the battery 510 may be a "point-of-use" battery that may be activated upon alignment or interdigitation of its electrodes and exposure to ambient air. In some aspects, the battery 510 may remain dormant for relatively long periods of time (such as three or more years), thereby increasing the shelf-life of the battery 510, for example, compared to conventional batteries.

In various implementations, the battery 510 may be disposable. In some aspects, the battery 510 may include a barrier layer disposed over the air opening 535 formed in the cathode 530. The barrier layer, not shown in FIG. 5 for simplicity, may be one example of the barrier layer 160 described with reference to FIG. 1. That is, the barrier layer can prevent water vapor, gaseous oxygen, and other reactants present in the ambient air from entering interior portions of the battery 510 and reacting with each other and/or various exposed carbon surfaces of the cathode 530. Since activation of the battery 510 is possible only after interior portions of the battery 510 are exposure to ambient air, 3D printed metal air batteries constructed in accordance with various aspects of the present disclosure can remain dormant for relatively long periods of time.

Figure 6:
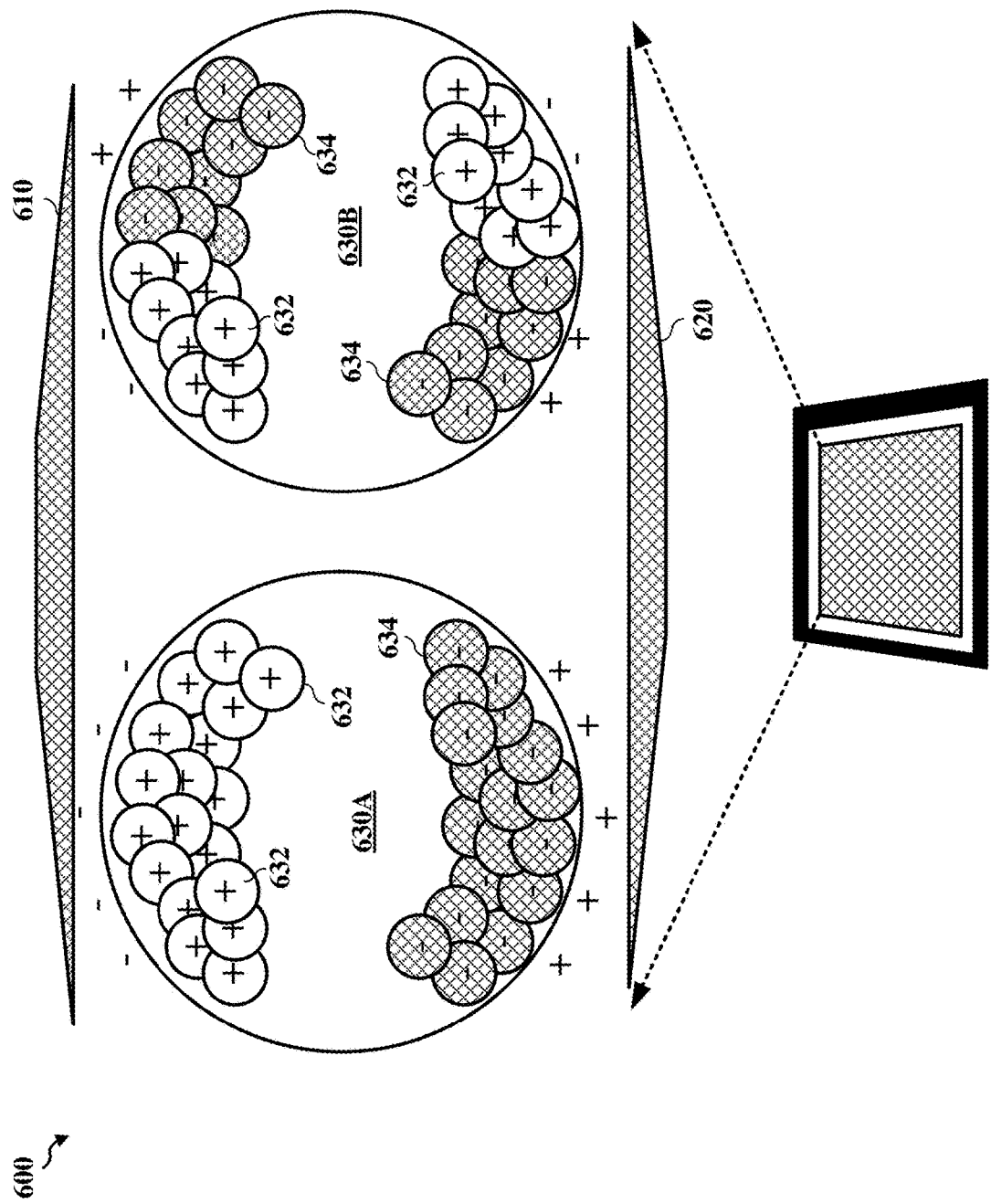
FIG. 6 shows an electrophoretic display (EPD), according to some implementations.

FIG. 6 shows a schematic view of an electrophoretic display (EPD) 600, according to some implementations. In some aspects, the display 600 may be affixed to a container such as (but not limited to) the container 502 of FIG. 5, for example, to display information pertaining to the contents of the container 502. The display 600 may include a first conducting electrode panel 610, a second conducting electrode panel 620, and a number of microcapsules 630A-630B (only two microcapsules shown for simplicity). The electrode panels 610 and 620 are positioned parallel relative to each other, and may be configured to receive an electric potential. In some implementations, the electrode panels 610 and 620 may be transparent so that the microcapsules 630A-630B are exposed to visible light in a surrounding environment.

Each of microcapsules 630A-630B may be filled with a plurality of positively charged white pigment particles 632 and a plurality of negatively charged black pigment particles 634. In some implementations, a voltage may be applied between or across the electrode panels 610 and 620 to selectively move the positively charged white pigment particles 632 and/or the negatively charged black pigment particles 634 toward one of the electrode panels 610 or 620. For example, when a first voltage is applied between the electrode panels 610 and 620 such that the potential of the first electrode panel 610 is more negative than the potential of the second electrode panel 620, the positively charged white pigment particles 632 may move to towards the first electrode panel 610 and the negatively charged black pigment particles 634 may move to towards the second electrode panel 620, for example, as shown in the first microcapsule 630A. For another example, when a second voltage is applied between the electrode panels 610 and 620 such that the potential of the first electrode panel 610 is approximately equal to the potential of the second electrode panel 620, some of the positively charged white pigment particles 632 and some of the negatively charged black pigment particles 634 may move towards the first electrode panel 610, and others of the positively charged pigment particles 632 and others of the negatively charged black pigment particles 634 may move towards the second electrode panel 620.

Accordingly, either positively charged white particles 632 or negatively charged black particles 634 may be visible on a EPD screen including the first and second panels 610 and 620, respectively. In contrast to backlit displays, visible light incident upon top portions of the microcapsules 630A and 630B may be either scattered to create white pigmentation or absorbed to create black pigmentation. In some aspects, the EPD 600 may be manufactured as a color EPD display by using, for example, a color filter. The color filter may divide each pixel into different colors including red, green, and blue (RGB) or red, green, blue, and white (RGBW).

Figure 7A:
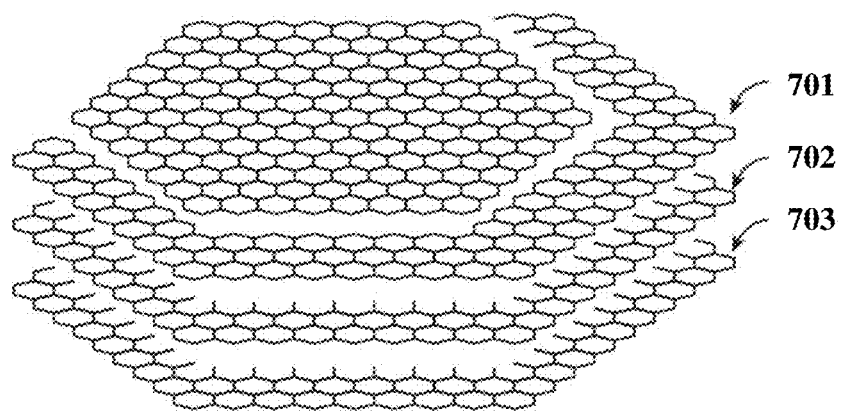
FIG. 7A is an illustration depicting stacked graphene nanoplatelets, according to some implementations.

FIG. 7A shows a graphene structure 700, according to some implementations. The graphene structure 700 is shown to include three graphene nanoplatelets 701-703 stacked on top of one another. In some implementations, the graphene nanoplatelets 701-703 may be self-nucleated and/or grown in a chemical reactor such as, for example, one of the microwave-based or thermal reactors described in commonly-owned U.S. Pat. No. 9,767,992. In some aspects, each of the graphene nanoplatelets 701-703 may have a thickness between 1 and 3 nanometers (nm), and may have diameter or width between approximately 100 nm and 100 microns. In some aspects, the graphene structure 700 may be used to construct the cathode 120 of the metal air battery 100 of FIG. 1. In other some aspects, the graphene structure 700 may be used to construct the cathode 230 of the air battery 200 of FIG. 2.

Figure 7B:
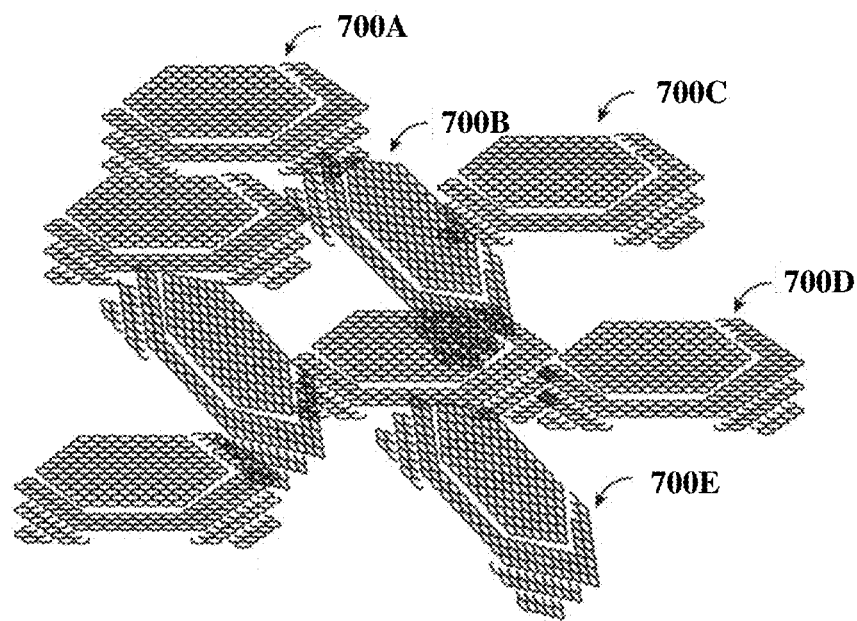
FIG. 7B is an illustration depicting an example growth of graphene nanoplatelets, according to some implementations.

FIG. 7B shows a graphene aggregate 750, according to some implementations. The graphene aggregate 750 may be formed by fusing a plurality of the graphene structures 700 of FIG. 7A together in an organized manner (for simplicity, only five of the graphene structures 700A-700E are labeled in the example of FIG. 7B. In some implementations, the graphene aggregate 750 may be synthesized in a chemical reactor such as, for example, one of the microwave-based or thermal reactors described in commonly-owned U.S. Pat. No. 9,767,992. In some aspects, the graphene aggregate 750 may be synthesized from an atmospheric plasma-based vapor flow stream. Synthesis of the graphene aggregate 750 may occur either in-flight to nucleate from an initially formed carbon-based homogenous nucleation, or may occur during deposition onto a substrate. In this way, the graphene aggregate 750 can be grown in an organized manner that results in the graphene aggregate 750 having an ornate structure independent of seed particles conventionally used for nucleation.

Specifically, the production of graphene using graphitic exfoliation may require usage of graphite as a starting material. Graphite, a conductive material, may be used as an electrode in batteries and other electrochemical devices. In addition to its function as an inert electrode, electrochemical methods have been employed to form graphite intercalation compounds (GICs) and, more recently, to exfoliate graphite into few-layered graphene. Exfoliation, as generally understood and as referred to herein, implies—in an intercalation chemistry related context—the complete separation of layers of material, and typically requires aggressive conditions involving highly polar solvents and aggressive reagents. Electrochemical methods are attractive as they eliminate the use of chemical oxidants as the driving force for intercalation or exfoliation, and an electromotive force is controllable for tunable GICs. More importantly, the extensive capabilities of electrochemical functionalization and modification enable the facile synthesis of functional graphene and its value-added nanohybrids.

Unlike exfoliation, including thermal exfoliation of graphite to produce graphene, the graphene aggregate 750 may be synthesized by self-nucleation from a carbon-inclusive gaseous species flowed into a reactor under controlled conditions. In some instances, the gaseous species may include methane ($CH_4$), which may be flowed into a reaction chamber of a chemical reactor. Upon receipt of energy, such as that provided by electromagnetic radiation and/or thermal energy, incoming gaseous species may spontaneously crack to form highly reactive carbon-inclusive radical species. These radical species may freely recombine within the reactor to generate allotropes with other cracked carbons and create an initial carbon-based site, which facilitates additional particles that grow or nucleate from defects of the initially formed particle or orthogonally fuse or sinter additional carbon-based particles.

Figure 8A:
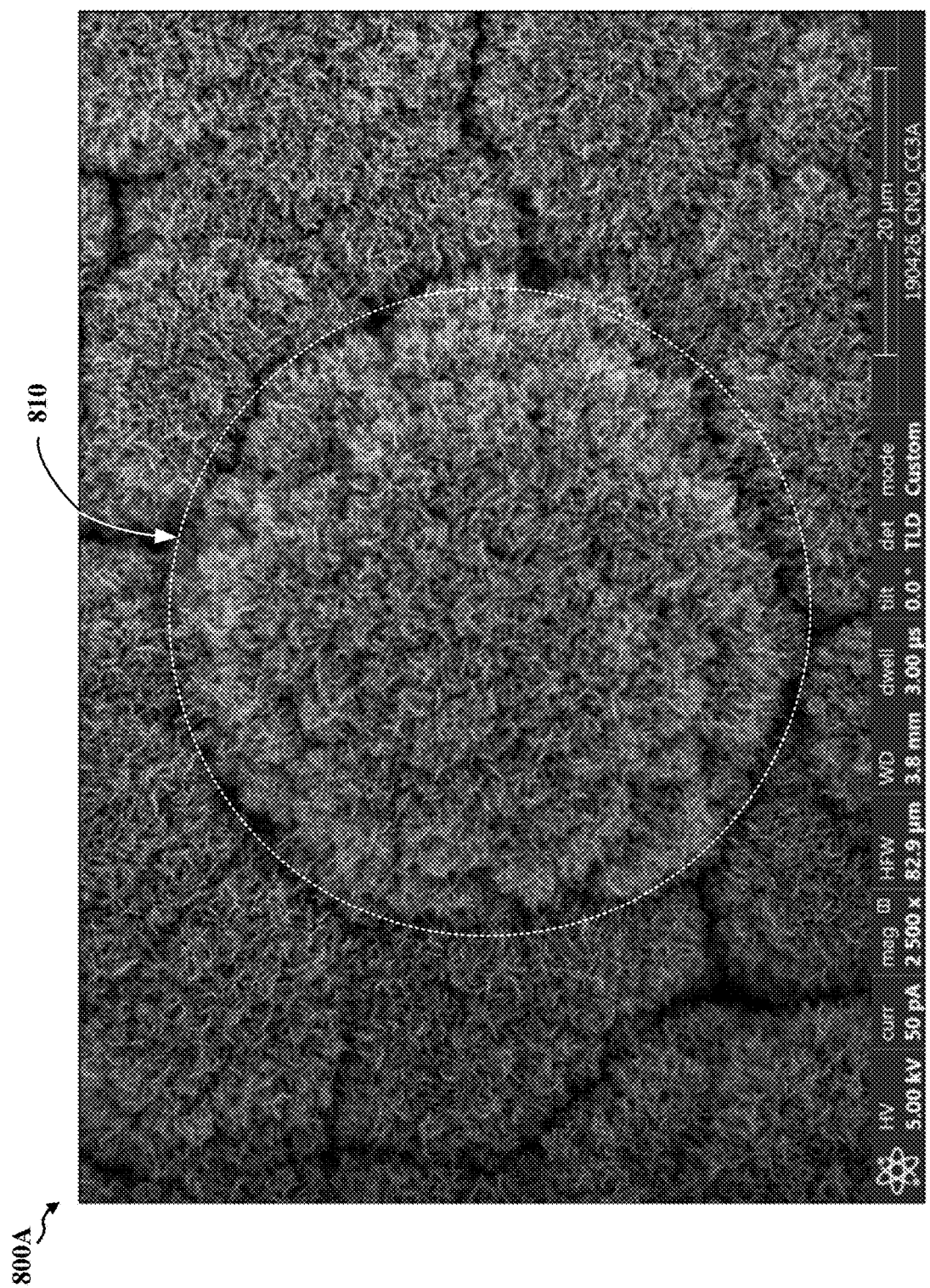
FIGS. 8A-8F shows micrographs of carbon-based structures that may be used in an cathode of a battery, according to some implementations.
Figure 8B:
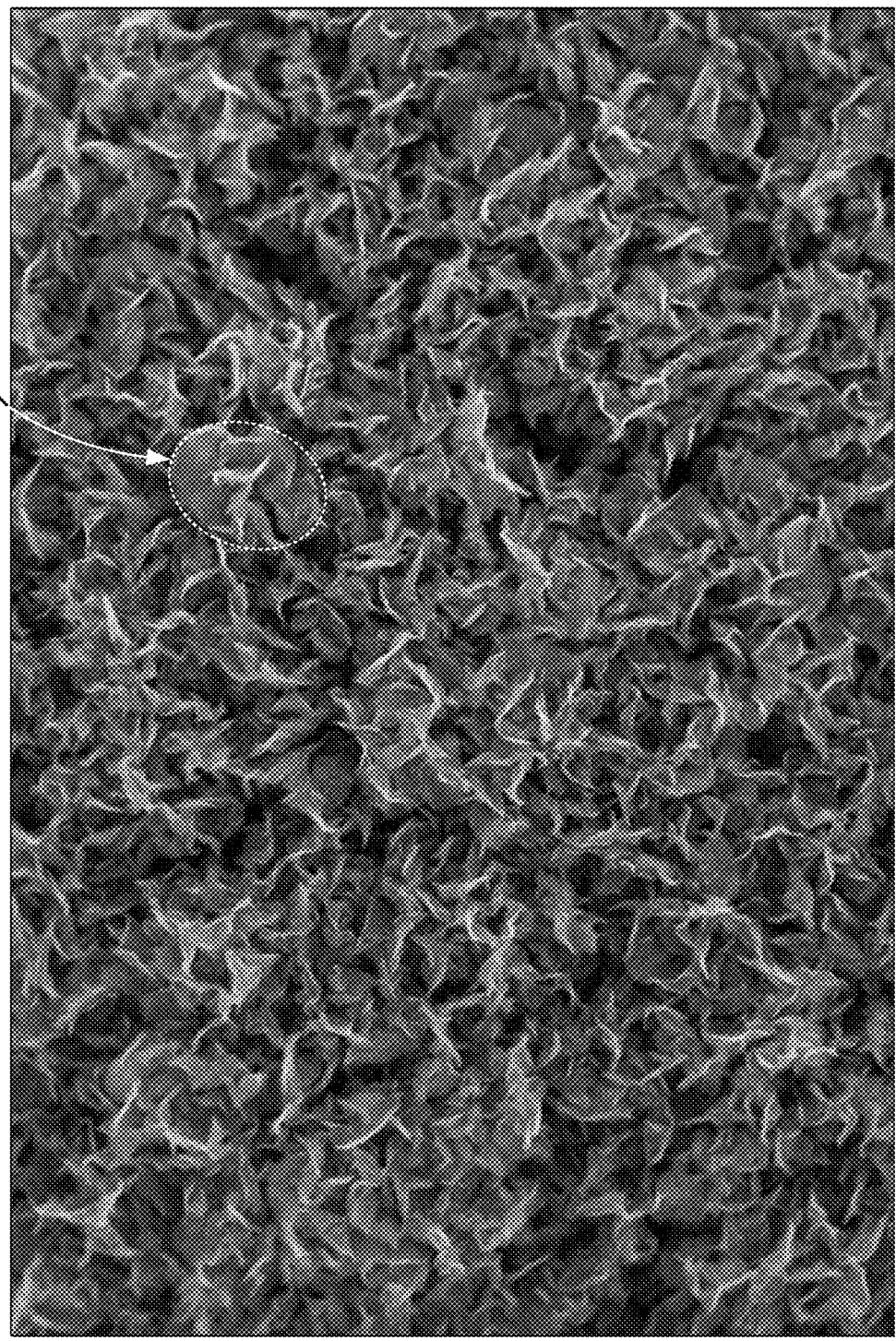

FIG. 8A shows a micrograph 800A of example carbon-based particles 810, according to some implementations. FIG. 8B shows an enlarged portion 800B of the carbon-based particles 810 of FIG. 8A. As shown, the carbon-based particles 810 have an internal porosity and microstructure that can be formed during in-flight nucleation in a microwave plasma-based reactor, for example, to create 3D mesoporous carbon-based particles. The carbon-based particles 810 may include one or more layers of carbon-containing platelets joined to one another at corresponding non-concentric co-planar junctions. In some implementations, the platelets within a first layer may be oriented relative to each other at one or more first angles, and the platelets within a second layer may be oriented relative to each other at one or more second angles that are different than the first angles. In some instances, the platelets of the first layer may be rotated by 90 degrees relative to the platelets of the second layer. The carbon-based particles 810 can be grown to form agglomerations, which can be lithiated to form the textured scaffold 300 of FIG. 3. As discussed, the carbon scaffold 700 can be used to form cathodes such as (but not limited to) the cathode 130 of FIG. 1 or the cathode 230 of FIG. 2.

Figure 8C:
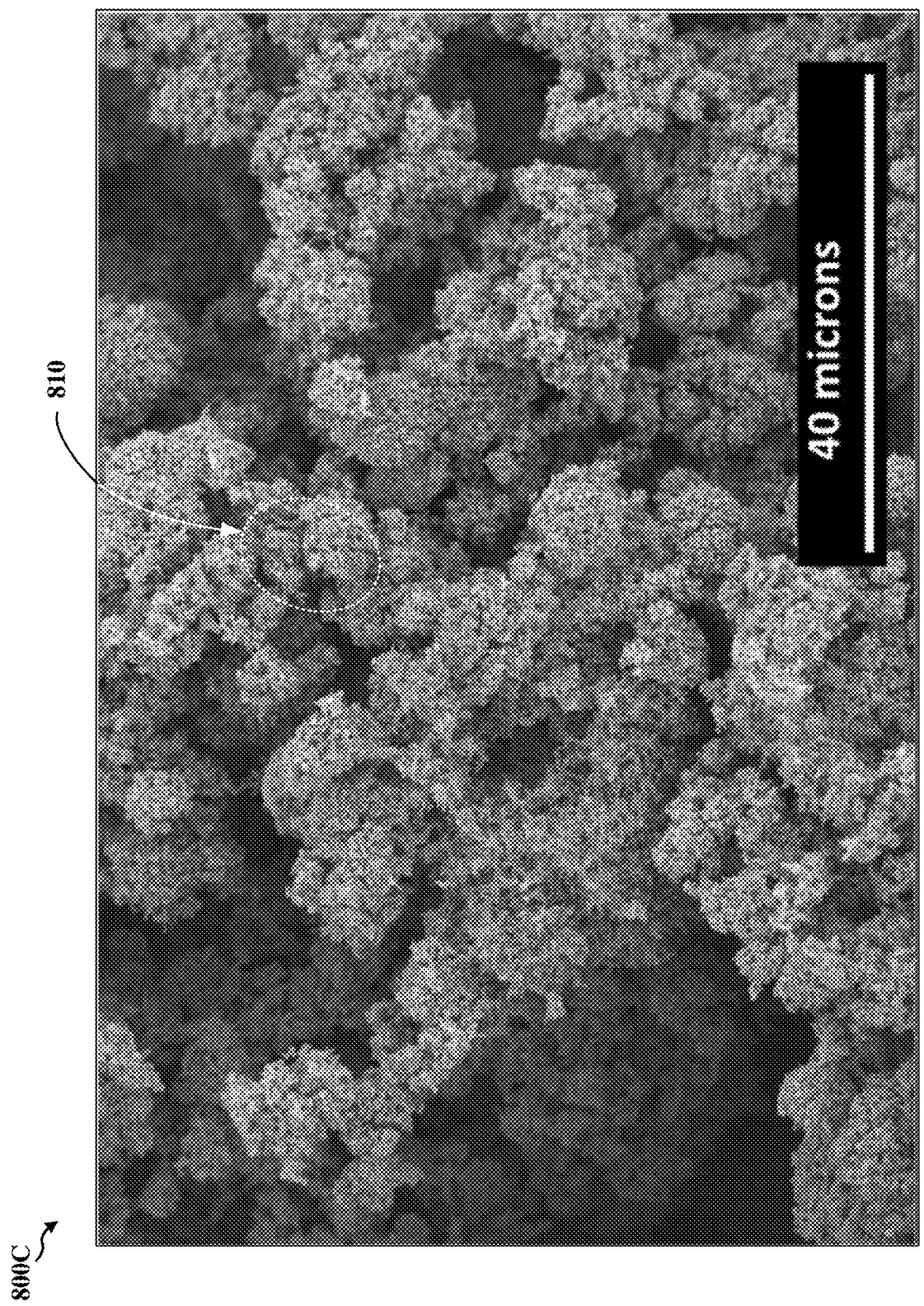
Figure 8D:
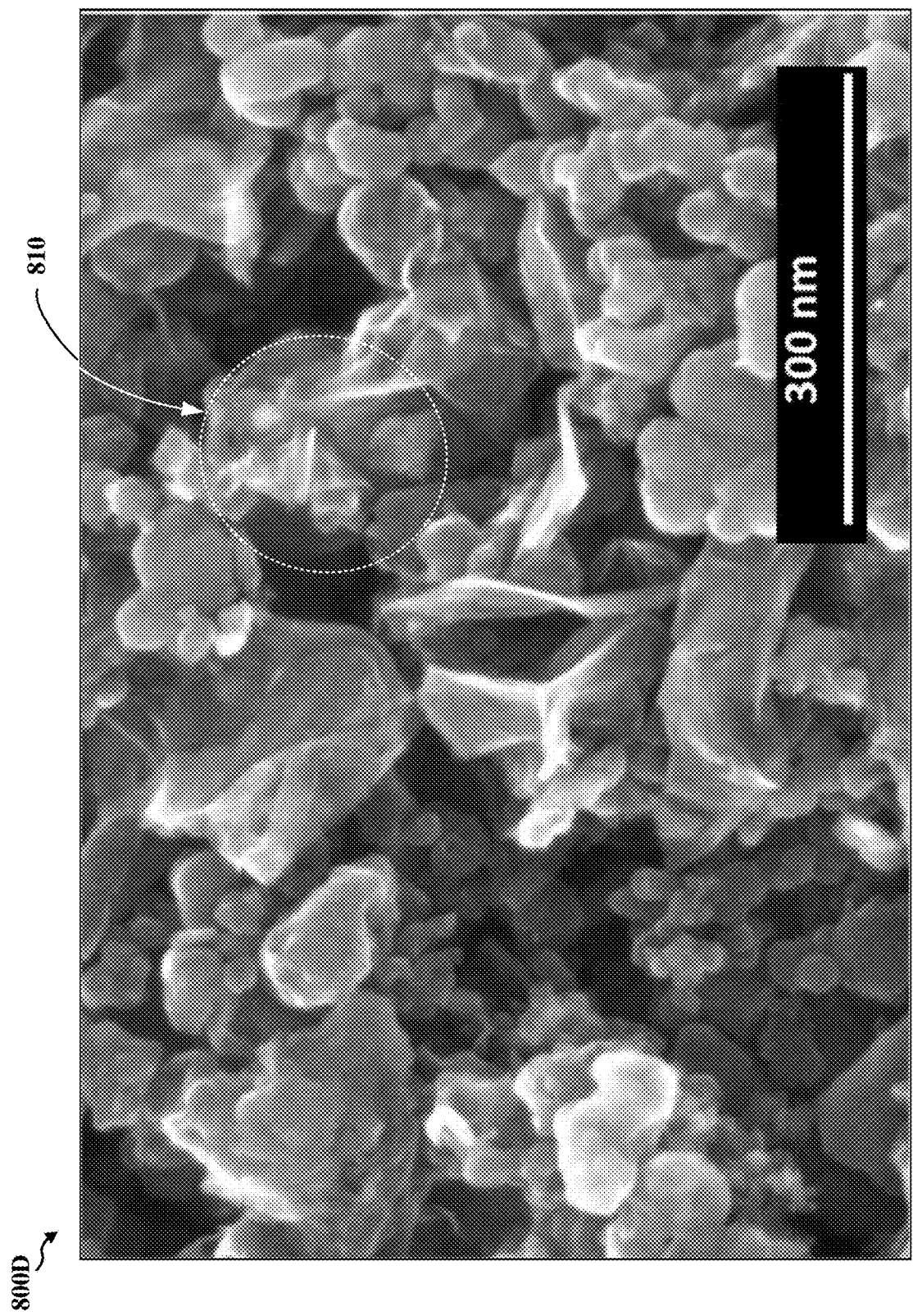
Figure 8E:
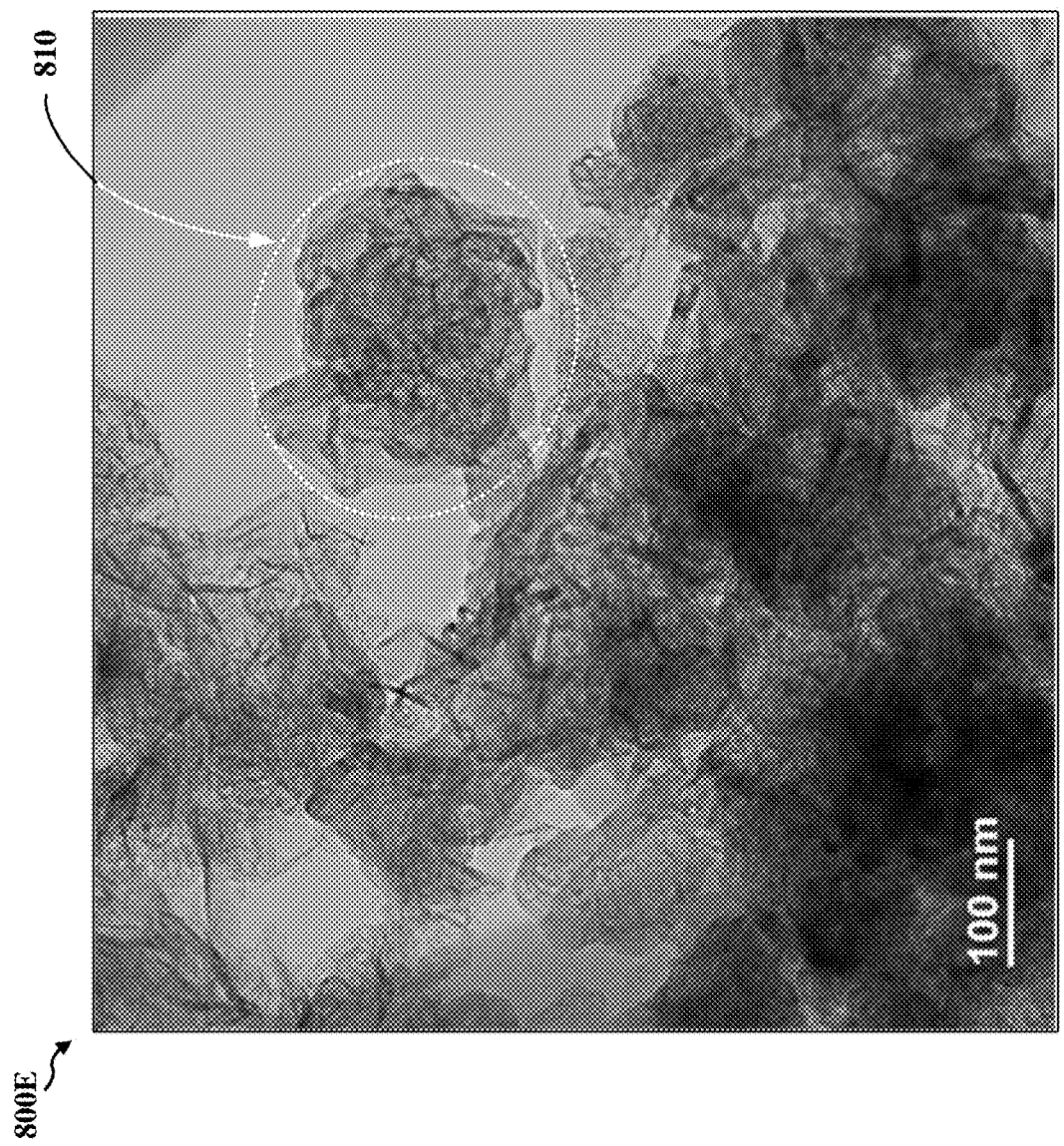
Figure 8F:
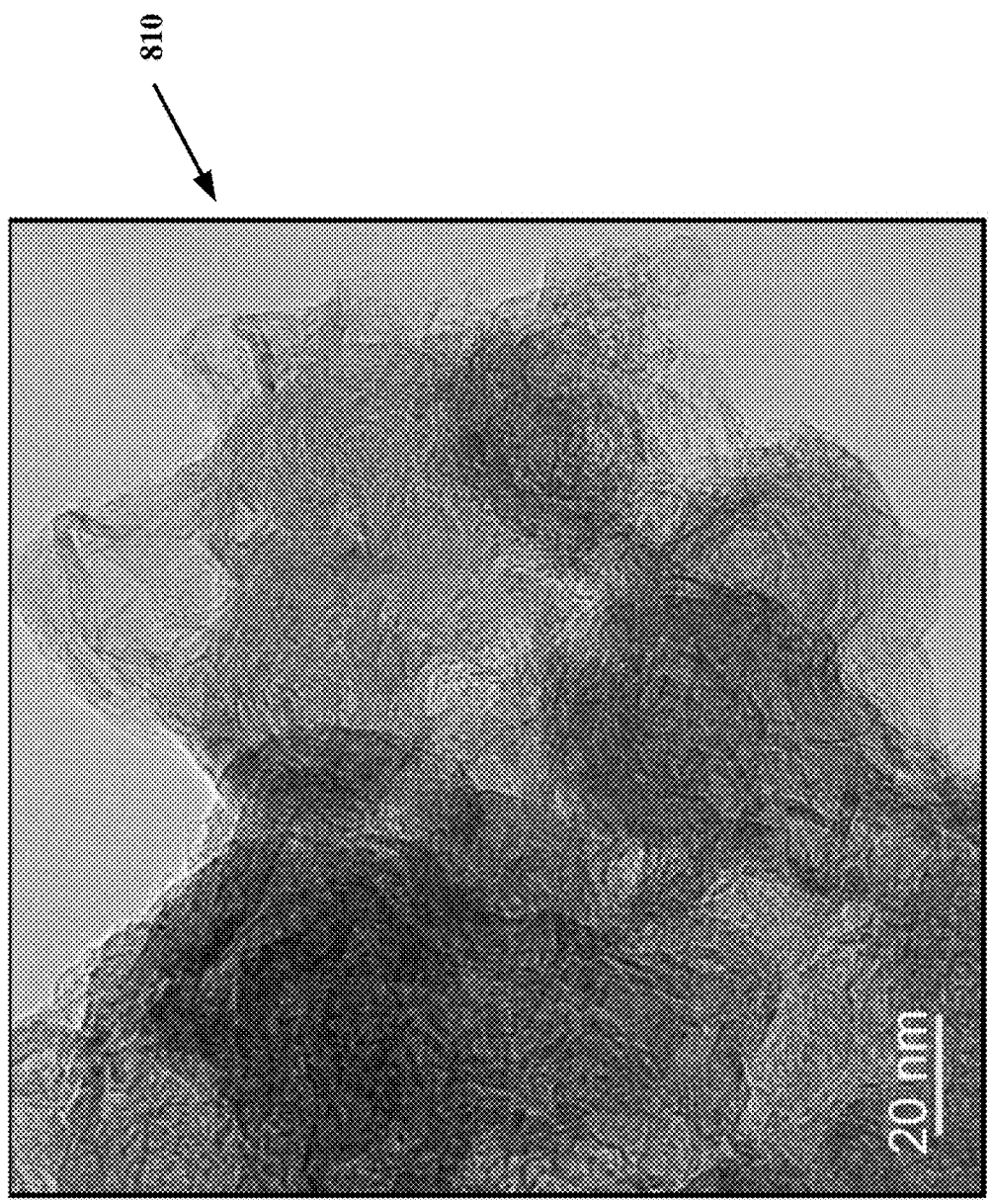

FIG. 8C shows an SEM image 800C of the carbon-based particles 810 relative to a 40 micron scale, FIG. 8D shows an SEM 800D image of the carbon-based particles 810 relative to a 300 nm scale, FIG. 8E shows a transmission electron microscope (TEM) image 800E of the carbon-based particles 810 relative to a 100 nm micron scale, and FIG. 8F shows a TEM image 800F of the example carbon-based particles 810 relative to a 20 nm scale, according to some implementations. As shown, the carbon-based particles 810 include 3D mesoporous carbon allotropes having a hierarchical graphene structure with a specific edge-to-basal plane ratio. In some aspects, the edge-to-basal plane ratio for the graphene in the present particulate carbon is about 1:10, or about 1:100, or from 1:10 to 1:100. The carbon-based particles 810 have a surface area of approximately 85.9 m2/g as measured using a nitrogen BET method, and have a surface area of approximately 93.5 m2/g as measured by the density functional theory (DFT) method.

The carbon-based particles 810 contain graphene, and have greater purities and electrical conductivities than conventionally produced carbon materials. The carbon-based particles 810 also have Raman signatures indicating a high degree of order, and do not contain seed particles. In some embodiments, the carbon-based particles 810 may contain doped carbon materials (e.g., carbon doped with H, O, N, S, Li, Cl, F, Si, Se, Sb, Sn, Ga, As, and/or other metals), undoped carbon materials, or any combination thereof. The carbon-based particles 810 can also include carbon with a matrix allotrope doped with carbon atoms (not in the matrix structure) and/or doped with other types of carbon allotropes. The carbon-based particles 810 can also be doped with functional groups, such as amine (NH3) groups. In some embodiments, the carbon-based particles 810 may be formed using a dopant material introduced within a gas, liquid, or colloidal dispersion, which is provided to a chemical reactor and doped. In some aspects, the dopant materials can be combined with a hydrocarbon precursor material and cracked in a microwave plasma reactor or a thermal reactor. As an example, silicon can be input into a reactor along with a hydrocarbon process gas (or other carbon-containing process material such as a liquid alcohol) to produce silicon nano-mixed with graphene, graphene-based carbon materials, and/or other carbon allotropes. In other examples, the resulting nano-mixed particulate carbon of the present embodiments can contain particles of O, S, LixSy (where x=0-2 and y=1-8), Si, $Li_{22}Si_5$, $Li_{22\text{-}x}Si_5\text{-}y$ (where x=0-21.9, and y=1-4.9), and $Li_{22\text{-}x}Si_{5\text{-}y\text{-}z}M_z$ (where x=0-21.9, y=1-4.9, z=1-4.9, and M is one or more of S, Se, Sb, Sn, Ga, or As).

In other embodiments, the carbon-based particles 810 may contain nano-mixed particulate carbon. The surface area, structure, and/or surface activity of these carbon-based particles 810 can be tuned by nano-mixing the carbon particles with the particles of one or more other materials. For example, the particles of a nano-mix additive material can be integrated within the particles of the graphene-based carbon. The average diameter of the particles of the nano-mix additive material and the graphene-based carbon materials in the nano-mixed particulate carbon may be between approximately 1 nm and 1 micron, between approximately 1 nm and 500 nm, between approximately 1 nm and 100 nm, or as small as 0.1 nm. In some aspects, the nano-mixing involves introducing nano-mix additives during particulate formation (e.g., during a hydrocarbon cracking process in a microwave plasma reactor or in a thermal reactor) such that the nano-mix additive material is integrated into the graphene-based carbon material as the carbon material is produced, rather than combining a carbon raw material with an additive in a later process as in certain conventional methods.

In some implementations, the carbon-based particles 810 may be post-processed to reduce the particle size without damaging the carbon allotropes contained within. Some example post-processing techniques include (but are not limited to) ball milling, grinding, attrition milling, microfluidizing, jet milling, shear mixing, chemical etching, oxidizing (e.g., Hummer method), thermal annealing, doping by adding elements during annealing (e.g., O, S, Li, Si, Se, Sb, Sn, Ga, As, and/or other metals), steaming, filtering, and lypolizing, and the like. In addition, one or more sintering processes such as Spark Plasma Sintering, Microwave, and Ultra-Violet can also be used.

In some other implementations, the particulate carbons described herein can be combined with other materials to create composite films. For one example, solid carbon particles having a size between approximately 0.3 microns and 40 microns and polymer beads are combined at a ratio of 90:10 to form a mixture that can be cast onto a substrate and then treated in a suitable oven such as (but not limited to) an inert gas oven, a reactive gas oven, or a vacuum oven. For another example, the mixture can be combined with a solvent to form an ink, which can then be deposited onto a substrate via casting or printing. For another example, particulate carbon can be encapsulated with a polymer to form colloidal core-shell structures that can be printed onto any suitable surface via inkjet printing, aerosol spray coating, spin coating, or roll coating.

In some implementations, the carbon-based particles 810 may be synthesized through self-assembly independent of a binder to feature multi-modal dimensions. These dimensions may include various orifices, conduits, voids, pathways, and/or conduits defined to have a specific dimension, such as being mesoporous. A mesoporous material is a material containing pores with diameters between 2 and 50 nm, according to IUPAC nomenclature. For the purposes of comparison, IUPAC defines microporous material as a material having pores smaller than 2 nm in diameter and macroporous material as a material having pores larger than 50 nm in diameter. Mesoporous materials may include various types of silica and alumina that have similarly sized mesopores. Mesoporous oxides of niobium, tantalum, titanium, zirconium, cerium, and tin may be implemented in various configurations of the batteries disclosed herein. Of the variants of mesoporous materials, mesoporous carbon, such as carbons and carbon-based materials have voids, orifices, pathways, conduits or the like having at least one mesoporous dimension, has achieved particular prominence, having direct applications in energy storage devices. Mesoporous carbon can be defined as having porosity within the mesopore range, and this significantly increases the specific surface area.

Another common mesoporous material is activated carbon, which is a form of carbon processed to have small, low-volume pores that increase the surface area. Activated carbon, in a mesoporous context, is typically composed of a carbon framework with mesoporosity and microporosity, such as depending on the conditions under which it was synthesized. According to IUPAC, a mesoporous material can be disordered or ordered in a mesostructure. In crystalline inorganic materials, mesoporous structure noticeably limits the number of lattice units, and this significantly changes the solid-state chemistry. For example, the battery performance of mesoporous electroactive materials is significantly different from that of their bulk structure.

Processes related to synthesis and/or growth of the carbon-based particles 810 within a reaction chamber are described in commonly-owned U.S. Pat. No. 9,767,992, the entirety of which is incorporated by reference herein. Synthesis can occur in systems other than microwave reactors, such as taking place in a thermal reactor. Thermal reactors refer to chemical reactors having enclosed volume in which a temperature-dependent chemical reactor occurs. In some implementations, the hydrocarbon gas flowed into a reactor for creation of the carbon-based particles 810 may be a short-chain hydrocarbon gas, while in other aspects, the hydrocarbon gas flowed into the reactor may be a long-chain hydrocarbon gas. In some instances, the hydrocarbon gas may include methane ($CH_4$) and/or butane ($C_4H_{10}$). In various implementations, the generation of suitable carbon-based radicals from a non-thermal equilibrium plasma for the creation of the carbon-based particles 810 may be based one or more of an input carbon-containing gas flow rate of 100 standard cubic centimeters per minute (scc/m)-5 standard liters per minute (slm); preference for lower flow rates when enhanced fidelity and tunability are desired; and preference for higher flow rates when higher output is desired.

In some implementations, the carbon-based particles 810 may be created based on the example recipe below:
pump-down the reactor to 50 mT and preclean/purge with Ar gas, repeat for 3 cycles;
activate gas flows as follows for purge/preclean using: $H_2$ at 15 standard cubic centimeters per second (sccm/s), Ar at 20 sccm/s;
activate microwave (MW) power of the reactor at 1700 W;
perform/run preclean operations for a duration of 15 min;
activate/alter gas flows for deposition using: $CH_4$ at 16 sccm/s, $H_2$ at 45 sccm/s, Ar at 61 sccm/s;
maintain MW power at 1700 W;
perform deposition operations for 30 min;
deactivate MW power and $CH_4$ gas flows; and
cool newly-formed carbon-based particles 810 in a $H_2$ and Ar rich environment for approximately 1 hr.

In some implementations, the carbon-based particles 810 may include nanoparticles that contain multi-walled spherical fullerenes (MWSFs) having a high uniformity (such as a ratio of graphene to MWSF between approximately 20% and 80%), having a high degree of order (such as a Raman signature with an ID/IG ratio between approximately 0.95 and 1.05), and a high degree of purity (such as the ratio of carbon to other elements, other than hydrogen, greater than 99.9%). In some instances, the MWSFs do not contain a core composed of impurity elements other than carbon.

In various implementations, the carbon nanoparticles and aggregates described herein may be characterized by Raman spectroscopy that is indicative of the high degree of order and uniformity of structure. In some implementations, the uniform, ordered and/or pure carbon nanoparticles and aggregates described herein are produced using reactors and methods, as described below.

As used herein, the term "graphene" refers to an allotrope of carbon in the form of a two-dimensional, atomic-scale, hexagonal lattice in which one atom forms each vertex. The carbon atoms in graphene are sp2 bonded. Additionally, graphene has a Raman spectrum with two main peaks that include a G-mode at approximately 1580 $cm^{-1}$ and a D mode at approximately 1350 $cm^{-1}$ when using a 532 nm excitation laser.

The term "fullerene" refers to a molecule of carbon in the form of a hollow sphere, ellipsoid, tube, or other shapes. Spherical fullerenes can also be referred to as Buckminsterfullerenes, or buckyballs. Cylindrical fullerenes can also be referred to as carbon nanotubes. Fullerenes are similar in structure to graphite, which is composed of stacked graphene sheets of linked hexagonal rings. Fullerenes may also contain pentagonal (or sometimes heptagonal) rings.

The term "multi-walled fullerene" refers to fullerenes with multiple concentric layers. For example, multi-walled nanotubes (MWNTs) contain multiple rolled layers (concentric tubes) of graphene. Multi-walled spherical fullerenes (MWSFs) contain multiple concentric spheres of fullerenes.

The term "nanoparticle" refers to a particle that measures from 1 nm to 989 nm. The nanoparticle can include structural characteristics, such as crystal structure, defect concentration, etc., and various types of atoms. The nanoparticle can be any shape, including but not limited to spherical shapes, spheroidal shapes, dumbbell shapes, cylindrical shapes, elongated cylindrical type shapes, rectangular prism shapes, disk shapes, wire shapes, irregular shapes, dense shapes (such as with few voids), porous shapes (such as with many voids), etc.

The term "aggregate" refers to a plurality of nanoparticles that are connected together by Van der Waals forces, by covalent bonds, by ionic bonds, by metallic bonds, or by other physical or chemical interactions. Aggregates can vary in size considerably, but in general are larger than about 500 nm.

A carbon nanoparticle refers to a nano-scale particle that includes two or more connected multi-walled spherical fullerenes (MWSFs) and layers of graphene coating the connected MWSFs such that MWSFs do not contain a core composed of impurity elements other than carbon. Nanoparticles containing connected MWSFs can have an average diameter in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm. The carbon nanoparticles can be combined to form carbon aggregates, for example, having a diameter between approximately 10 and 500 µm, between approximately 50 and 500 µm, between approximately 100 and 500 µm, between approximately 250 and 500 µm, between approximately 10 and 250 µm, between approximately 10 and 100 µm, or between approximately 10 and 50 µm.

Raman spectroscopy can also be used to characterize the structure of MWSFs or connected MWSFs. The main peaks in the Raman spectra are the G mode and the D mode. The G mode is attributed to the vibration of carbon atoms in $sp^2$ hybridized carbon networks, and the D mode is related to the breathing of hexagonal carbon rings with defects. In some cases, defects may be present, yet may not be detectable in the Raman spectra. For example, if the presented crystalline structure is orthogonal with respect to the basal plane, the D peak will show an increase. Alternatively, if presented with a perfectly planar surface that is parallel with respect to the basal plane, the D peak will be zero.

When using 532 nm incident light, the Raman G mode is typically at 1582 $cm^{-1}$ for planar graphite, however, can be downshifted for MWSFs or connected MWSFs (such as down to 1565 $cm^{-1}$ or down to 1580 $cm^{-1}$). The D mode is observed at approximately 1350 $cm^{-1}$ in the Raman spectra of MWSFs or connected MWSFs. The ratio of the intensities of the D mode peak to G mode peak (such as the ID/IG) is related to the degree of order of the MWSFs, where a lower ID/IG indicates a higher degree of order. An ID/IG near or below 1 indicates a relatively high degree of order, and an ID/IG greater than 1.1 indicates a lower degree of order.

A carbon nanoparticle or a carbon aggregate containing MWSFs or connected MWSFs, as described herein, has a Raman spectrum with a first Raman peak at about 1350 $cm^{-1}$ and a second Raman peak at about 1580 $cm^{-1}$ when using 532 nm incident light. The ratio of an intensity of the first Raman peak to an intensity of the second Raman peak (such as the ID/IG) for the nanoparticles or the aggregates described herein is in a range from 0.95 to 1.05, or from 0.9 to 1.1, or from 0.8 to 1.2, or from 0.9 to 1.2, or from 0.8 to 1.1, or from 0.5 to 1.5, or less than 1.5, or less than 1.2, or less than 1.1, or less than 1, or less than 0.95, or less than 0.9, or less than 0.8.

One benefit of producing carbon aggregates from carbon nanoparticles, particularly with diameters in the ranges described above, is that aggregates of particles greater than 10 µm are easier to collect than aggregates of particles that are smaller than 500 nm. The ease of collection reduces the cost of manufacturing equipment used in the production of the carbon nanoparticles and increases the yield of the carbon nanoparticles. Additionally, particles greater than 10 µm in size pose fewer safety concerns compared to the risks of handling smaller nanoparticles, such as potential health and safety risks due to inhalation of the smaller nanoparticles. The lower health and safety risks, thus, further reduce the manufacturing cost.

In various implementations, a carbon nanoparticle can have a ratio of graphene to MWSFs between approximately 10% to 90%, between approximately 10% to 80%, between approximately 10% to 60%, between approximately 10% to 40%, between approximately 10% to 20%, between approximately 20% to 40%, between approximately 20% to 90%, between approximately 40% to 90%, between approximately 60% to 90%, or between approximately 80% to 90%.

The carbon aggregates disclosed herein have relatively large surface areas. In some instances, the carbon aggregates disclosed herein have a Brunauer, Emmett and Teller (BET) specific surface area from 10 to 200 $m^2/g$, or from 10 to 100 $m^2/g$, or from 10 to 50 $m^2/g$, or from 50 to 200 $m^2/g$, or from 50 to 100 $m^2/g$, or from 10 to 1,000 $m^2/g$.

The carbon aggregates disclosed herein have relatively high electrical conductivities. In some implementations, the carbon aggregates disclosed herein may be compressed into a pellet having various electrical conductivities and various densities. For example, the electrical conductivity of the pellets may be as low as 500 S/m and as high as 100,000 S/m, and the density of the pellets may be as low as 1 $g/cm^3$ and as high as 3 $g/cm^3$.

Carbon particles and aggregates containing graphite, graphene and amorphous carbon can be generated using a microwave plasma reactor system using a precursor material that contains methane, or contains isopropyl alcohol (IPA), or contains ethanol, or contains a condensed hydrocarbon (such as hexane). In some other examples, the carbon-containing precursors are optionally mixed with a supply gas (such as argon). The particles produced in this example contained graphite, graphene, amorphous carbon, and no seed particles. The particles in this example had a ratio of carbon to other elements (other than hydrogen) of approximately 99.5% or greater.

In one example, a hydrocarbon was the input material for the microwave plasma reactor, and the separated outputs of the reactor comprised hydrogen gas and carbon particles containing graphite, graphene, and amorphous carbon. The carbon particles were separated from the hydrogen gas in a multi-stage gas-solid separation system. The solids loading of the separated outputs from the reactor was from 0.001 g/L to 2.5 g/L.

In another example, 3D carbon growth on fibers can be achieved by introducing a plurality of fibers into the klystron powered ionizing reactor and using plasma in the microwave reactor to etch the fibers. The etching creates nucleation sites such that when carbon particles and sub-particles are created by hydrocarbon disassociation in the reactor, growth of 3D carbon structures is initiated at these nucleation sites. The direct growth of the 3D carbon structures on the fibers, which themselves are 3D in nature, provides a highly integrated, 3D structure with pores into which resin can permeate. This 3D reinforcement matrix (including the 3D carbon structures integrated with high aspect ratio reinforcing fibers) for a resin composite results in enhanced material properties, such as tensile strength and shear, compared to composites with fibers that have smooth surfaces and which smooth surfaces typically delaminate from the resin matrix.

Figure 9:
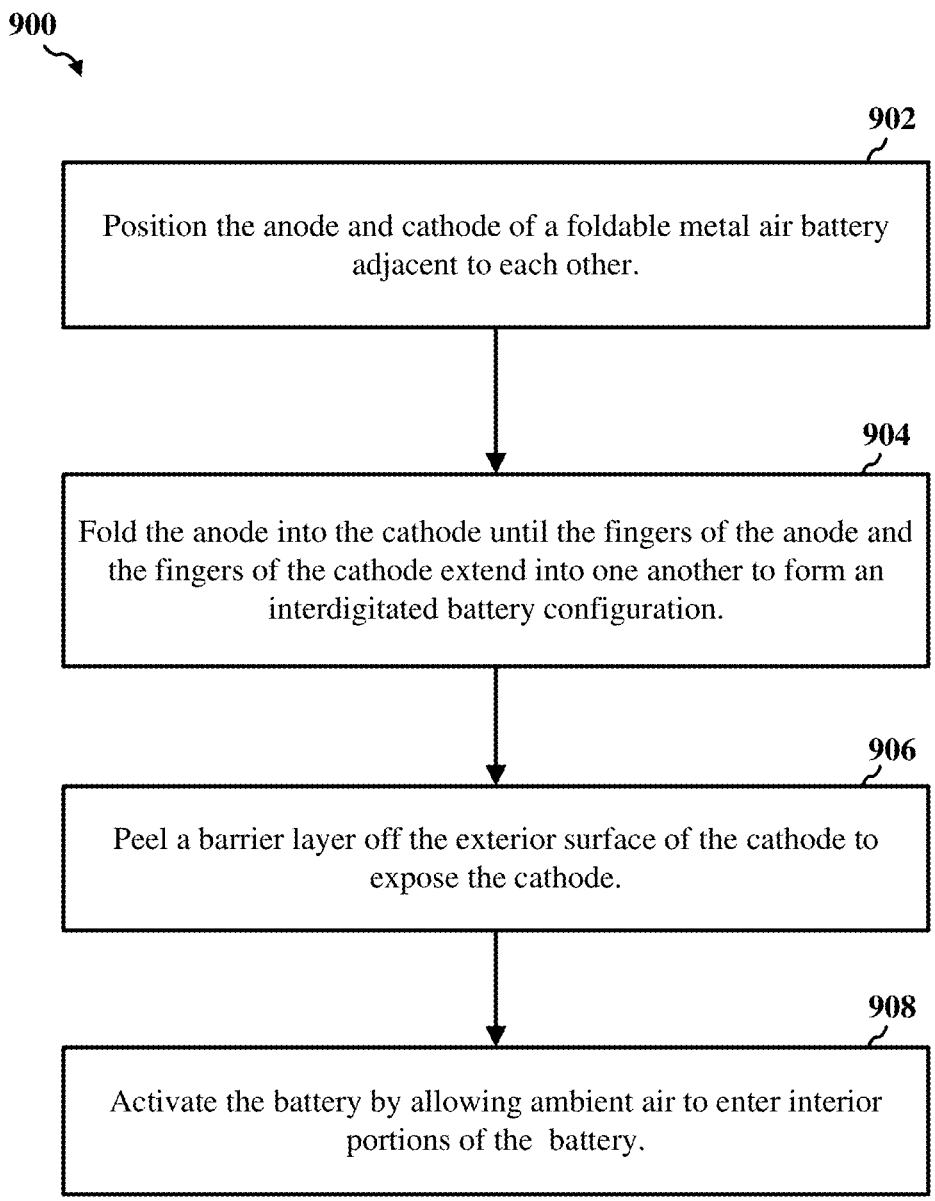
FIG. 9 shows a flowchart illustrating an example operation for assembling a foldable battery, according to some implementations.

FIG. 9 shows a flowchart illustrating an example operation 900 for assembling a foldable battery, according to some implementations. In various implementations, the foldable battery may be the battery 100 of FIG. 1, the battery 400 of FIG. 4, or the battery 510 of FIG. 5. In some implementations, the operation 900 may be performed by a user to assemble a container such as (but not limited to) a cardboard box. In some instances, the container may be the container 502 of FIG. 5.

In some implementations, the operation 900 begins at block 902 with positioning the anode and cathode of a foldable metal air battery adjacent to each other. The operation 900 continues at block 904 with folding the anode into the cathode until the fingers of the anode and the fingers of the cathode extend into one another to form an interdigitated battery configuration. The operation 900 continues at block 906 with peeling a barrier layer off the exterior surface of the cathode to expose an air opening. The operation 900 continues at block 908 with activating the battery by allowing ambient air to enter interior portions of the battery.

Figure 10:
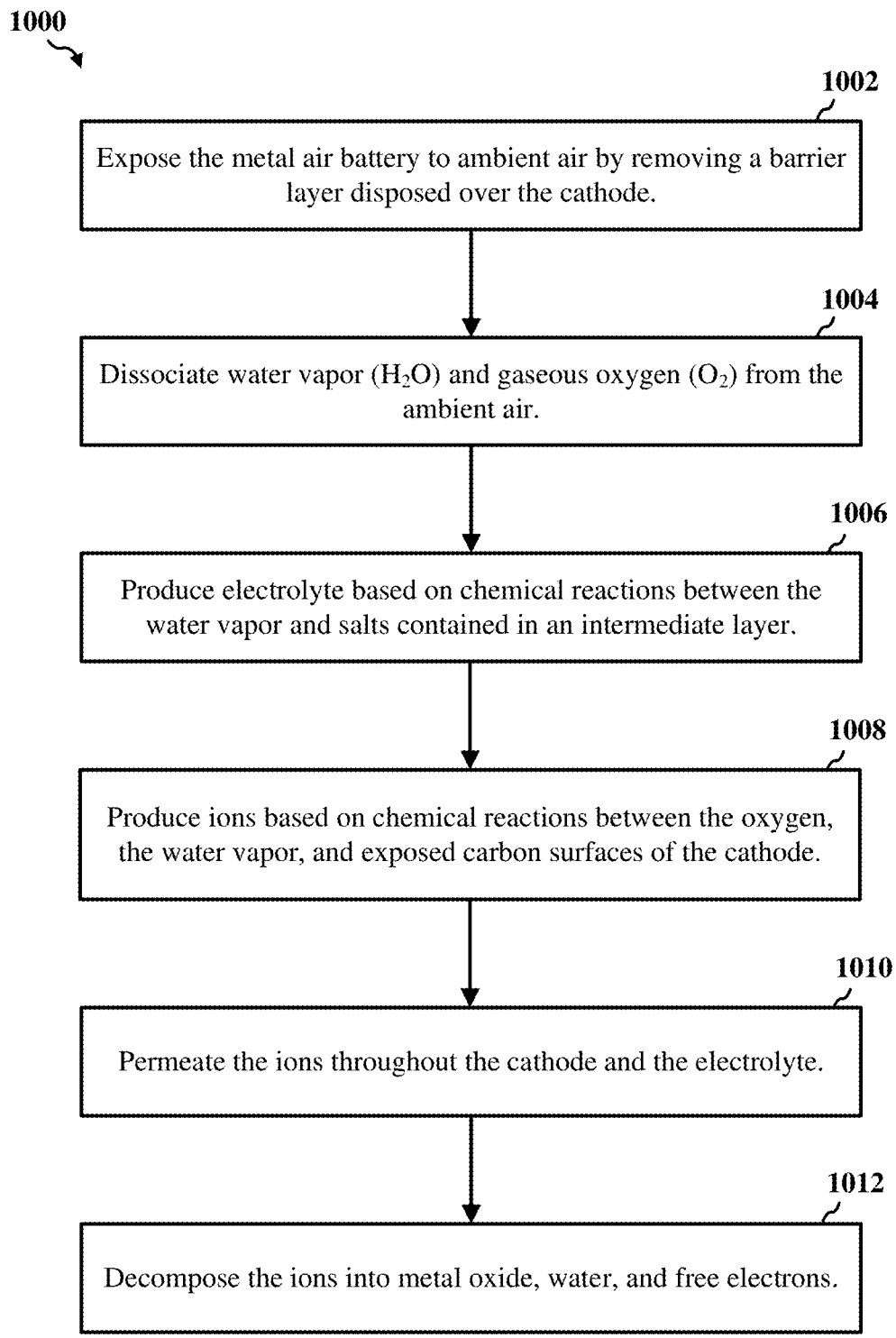
FIG. 10 shows a flowchart illustrating an example operation for activating a metal air battery, according to some implementations.

FIG. 10 shows a flowchart illustrating an example operation 1000 for activating a metal air battery, according to some implementations. In various implementations, the operation 1000 may be performed in conjunction with any suitable metal air battery including the metal air battery 100 of FIG. 1, the metal air battery 200 of FIG. 2, the metal air battery 410 of FIG. 4, or the metal air battery 510 of FIG. 5. In some implementations, the operation 1000 begins at block 1002 with exposing the metal air battery to ambient air by removing a barrier layer disposed over the cathode. In some instances, the cathode may be the cathode 130 of FIG. 1, the cathode 230 of FIG. 2, or the cathode 530 of FIG. 5. The barrier layer may be the barrier layer 160 described above with reference to FIG. 1.

The operation 1000 continues at block 1004 by dissociating water vapor ($H_2O$) and gaseous oxygen ($O_2$) from the ambient air. The operation 1000 continues at block 1006 with producing an electrolyte based on chemical reactions between the water vapor and salts contained in an intermediate layer. In some implementations, the intermediate layer may be a nano-fibrous membrane (NFM) such as (but not limited to) the NFM 140 of FIG. 1. In some instances, the salts may include sodium hydroxide (NaOH) or potassium hydroxide (KOH). In one implementation, the intermediate layer may also contain hygroscopic agents that can absorb water vapor supplied by the ambient air. In some instances, the hygroscopic agents may include one or more of glycerin/glycerol ($C_3H_8O_3$), ethanol ($C_2H_5OH$), methanol ($CH_3OH$), concentrated sulfuric acid ($H_2SO_4$), or concentrated sodium hydroxide (NaOH).

The operation 1000 continues at block 1008 with producing ions based on chemical reactions between the oxygen, the water vapor, and exposed carbon surfaces of the cathode. In some instances, the ions may include hydroxyl ($OH^-$) ions and/or zincate ions. The operation 1000 continues at block 1010 with permeating the ions throughout the cathode and the electrolyte. In some instances, the electrolyte may be provided by the intermediate layer (such as the NFM 140 of FIG. 1). The operation 1000 continues at block 1012 with decomposing the ions into metal oxide, water, and free electrons. In some instances, the metal oxide may include zinc oxide (ZnO).

Figure 11:
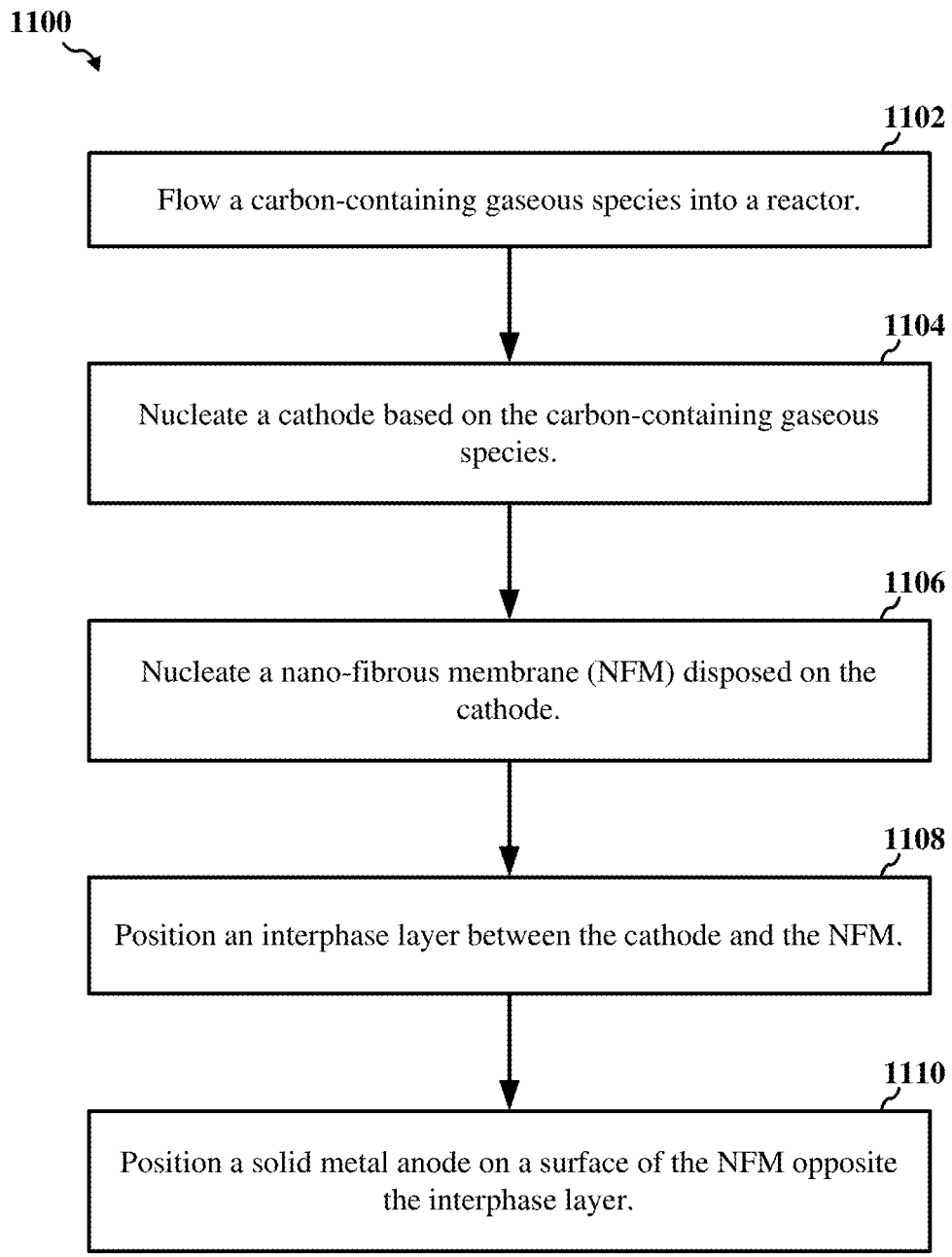
FIG. 11 shows a flowchart illustrating an example operation for manufacturing a metal air battery, according to some implementations.

FIG. 11 shows a flowchart illustrating an example operation 1100 for manufacturing a metal air battery, according to some implementations. In various implementations, the operation 1100 begins at block 1102 with flowing a carbon-containing gaseous species into a chemical reactor. In some implementations, the operation 1100 the chemical reactor may be one of the reactors described in U.S. Pat. No. 9,767,992, referenced above. The operation 1100 continues at block 1104 with nucleating a cathode based on the carbon-containing gaseous species of block 1102. In some implementations, the cathode may include a graded three-dimensional (3D) mesoporous-to-microporous open channeled graphene structure that includes a macroporous region opening up to the ambient air, a bi-modal mesoporous region extending from the macroporous region, and an N-doped microporous region extending from the bi-modal mesoporous region.

The operation 1100 continues at block 1106 with nucleating a nano-fibrous membrane (NFM) disposed on the cathode. In some implementations, the NFM may be formed by defining a framework to be impregnated by a salt and/or a hygroscopic agent, and defining a series of functionalized carbons coated onto the framework. The operation 1100 continues at block 1108 by positioning an interphase layer between the cathode and the NFM. The operation 1100 continues at block 1110 by positioning a solid metal anode on the NFM opposite the interphase layer.

As used herein, a phrase referring to "at least one of" a list of items refers to any combination of those items, including single members. As an example, "at least one of: a, b, or c" is intended to cover: a, b, c, a-b, a-c, b-c, and a-b-c. The various illustrative logics, logical blocks, modules, circuits, and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein but are to be accorded the widest scope consistent with this disclosure, the principles and the novel features disclosed herein.

What is claimed is:

1. A battery comprising:
   a metal anode and a cathode disposed on opposite sides of a body, the cathode comprising a carbon-based textured scaffold including a plurality of macroporous pathways configured to distribute oxygen and water vapor supplied by ambient air throughout the cathode and into interior portions of the body;
   a nano-fibrous membrane (NFM) disposed between the cathode and the metal anode, the NFM including one or more dry salts configured to produce a liquid electrolyte when exposed to water vapor delivered by the plurality of macroporous pathways of the cathode; and
   a hygroscopic interphase layer disposed between the cathode and the NFM, the hygroscopic interphase layer including a plurality of microporous pathways configured to drain excess quantities of the water vapor from the cathode and hydrate the one or more dry salts with the water vapor.

2. The battery of claim 1, wherein the NFM is coated with a layer of carbon-based particles including one or more of $sp^3$ diamond-like carbons or $sp^2$ graphene.

3. The battery of claim 1, wherein the NFM comprises a metal-organic framework (MOF) including poly(vinyl alcohol) (PVA), polyamide (PA), micro-crystalline cellulose (MCC), or any combination thereof.

4. The battery of claim 1, wherein the NFM includes hygroscopic agents configured to absorb the water vapor delivered by the plurality of macroporous pathways of the cathode.

5. The battery of claim 4, wherein the NFM is further configured to hydrate the one or more dry salts with the water vapor.

6. The battery of claim 4, wherein the one or more dry salts include one or both of sodium hydroxide (NaOH) or potassium hydroxide (KOH), and the hygroscopic agents include one or more of glycerin/glycerol ($C_3H_8O_3$), ethanol ($C_2H_5OH$), methanol ($CH_3OH$), concentrated sulfuric acid ($H_2SO_4$), or concentrated sodium hydroxide (NaOH).

7. The battery of claim 1, wherein the cathode is configured to guide transport of one or more ions in the liquid electrolyte in response to chemical reactions between the oxygen supplied by the ambient air and the water vapor.

8. The battery of claim 7, wherein one or more ions include hydroxide ($OH^-$) ions, zincate ($Zn(OH)_4^{2-}$) ions, or any combination thereof.

9. The battery of claim 1, wherein the NFM is formed of Chitosan or carboxymethyl cellulose (CMC).

10. The battery of claim 1, wherein the carbon-based textured scaffold includes a plurality of catalytic sites configured to participate in one or more of an oxidation chemical reaction or a reduction chemical reaction.

11. The battery of claim 10, wherein the plurality of catalytic sites are doped with manganese, manganese oxide (MnO), and platinum.

12. The battery of claim 1, wherein the plurality of macroporous pathways are defined within an outer region of the cathode and include pores formed in an exterior surface of the cathode.

13. The battery of claim 12, wherein the pores have a diameter greater than approximately 50 nanometers.

14. The battery of claim 12, wherein the carbon-based textured scaffold further includes a plurality of mesoporous pathways defined within an inner region of the cathode, the plurality of mesoporous pathways interconnected with the plurality of macroporous pathways and configured to drain excess water vapor from the cathode.

15. The battery of claim 14, wherein each mesoporous pathway has a diameter between approximately 2 and 30 nanometers.

16. The battery of claim 14, wherein the mesoporous pathways are defined by a plurality of N-doped graphene particles fused together.

17. The battery of claim 14, wherein the carbon-based textured scaffold is a graded three-dimensional (3D) macroporous-to-mesoporous open channeled graphene structure.

18. The battery of claim 14, wherein the inner region of the cathode further includes a plurality of microporous pathways connected to the mesoporous pathways and interconnected with the macroporous pathways.

19. The battery of claim 14, wherein the hygroscopic interphase layer has a thickness between approximately 2 and 10 nanometers, the inner region of the cathode has a thickness between approximately 0.1 and 50 microns, and the outer region of the cathode has a thickness between approximately 10 and 50 microns.

20. The battery of claim 1, wherein the carbon-based textured scaffold has a surface area greater than approximately 1,000 $m^2/g$.

21. The battery of claim 1, wherein the hygroscopic interphase layer includes the liquid electrolyte.

22. The battery of claim 1, wherein the carbon-based textured scaffold comprises a three-dimensional (3D) graphene structure.

23. The battery of claim 1, further comprising a barrier layer removably disposed over an exterior surface of the cathode.

24. The battery of claim 23, wherein the barrier layer is configured to prevent ambient air from entering interior portions of the battery through the plurality of macroporous pathways.

25. The battery of claim 24, wherein the barrier layer is configured to seal each of the plurality of macroporous pathways by at least partially covering the exterior surface of the cathode.

26. The battery of claim 24, wherein the battery is configured to be activated in response to a removal of the barrier layer from the exterior surface of the cathode.

27. The battery of claim 24, wherein removal of the barrier layer from the exterior surface of the cathode is configured to activate the battery by allowing the ambient air to enter interior portions of the battery through the plurality of macroporous pathways.

* * * * *